United States Patent
Rioux et al.

(10) Patent No.: US 7,691,078 B2
(45) Date of Patent: Apr. 6, 2010

(54) DRAINING BODILY FLUIDS WITH A STENT

(75) Inventors: Robert Rioux, Ashland, MA (US);
Christopher R. O'Keefe, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1303 days.

(21) Appl. No.: 11/179,110

(22) Filed: Jul. 11, 2005

(65) Prior Publication Data
US 2005/0273158 A1 Dec. 8, 2005

Related U.S. Application Data

(62) Division of application No. 09/862,270, filed on May 22, 2001, now Pat. No. 6,981,964.

(51) Int. Cl.
*A61N 1/30* (2006.01)
(52) U.S. Cl. .................................................. 604/19
(58) Field of Classification Search .............. 604/96.01, 604/104, 105, 160, 107, 108; 606/191–194, 606/198
See application file for complete search history.

(56) References Cited

U.S. PATENT DOCUMENTS

| | | | |
|---|---|---|---|
| 3,527,226 A | 9/1970 | Hakim et al. | |
| 3,657,744 A | 4/1972 | Ersek | |
| 3,923,066 A | 12/1975 | Francisoud et al. | 128/348 |
| 3,938,529 A | 2/1976 | Gibbons | |
| 4,156,067 A | 5/1979 | Gould | |
| 4,240,434 A | 12/1980 | Newkirk | |
| 4,307,723 A | 12/1981 | Finney | 128/349 |
| 4,423,725 A | 1/1984 | Baran et al. | |
| 4,655,771 A | 4/1987 | Wallsten | 623/1 |
| 4,660,560 A | 4/1987 | Klein | |
| 4,713,049 A | 12/1987 | Carter | 604/8 |
| 4,732,152 A | 3/1988 | Wallsten et al. | 128/343 |
| 4,768,507 A | 9/1988 | Fischell et al. | |
| 4,771,773 A | 9/1988 | Kropf et al. | |

(Continued)

FOREIGN PATENT DOCUMENTS

EP 0 274 846 7/1988

(Continued)

OTHER PUBLICATIONS

Duerig et al.; "An Overview of Superelastic Stent Design"; © 2000 Isis Medical Media Ltd.; (pp. 235-246).

(Continued)

*Primary Examiner*—Manuel A Mendez

(57) ABSTRACT

A stent for assisting urinary release in a male patient includes a first segment, a second segment, and a connecting member disposed between the first and second segments. The first segment includes a multi-winged malecot. When the stent is properly positioned within the patient's urinary system, the first segment is located on one side of the external sphincter with the multi-winged malecot located within the bladder to inhibit migration of the stent, and the second segment is located on the other side of the external sphincter and also tends to inhibit migration of the stent. The connecting segment is sized to extend through the external sphincter to couple the first and second segments together while not interfering with the normal operation of the external sphincter.

22 Claims, 34 Drawing Sheets

U.S. PATENT DOCUMENTS

| | | |
|---|---|---|
| 4,813,429 A | 3/1989 | Eshel et al. ............... 128/736 |
| 4,895,566 A | 1/1990 | Lee |
| 4,931,037 A | 6/1990 | Wetterman ....................... 604/8 |
| 4,932,938 A | 6/1990 | Goldberg et al. |
| 4,954,126 A | 9/1990 | Wallsten ....................... 600/36 |
| 4,955,859 A | 9/1990 | Zilber ............................ 604/8 |
| 4,973,301 A | 11/1990 | Nissenkorn ..................... 604/8 |
| 4,990,155 A | 2/1991 | Wilkoff |
| 4,994,066 A | 2/1991 | Voss ............................. 606/108 |
| 4,995,868 A | 2/1991 | Brazier ........................ 604/105 |
| 5,026,377 A | 6/1991 | Burton et al. ............... 606/108 |
| 5,037,427 A | 8/1991 | Harada et al. |
| 5,041,092 A | 8/1991 | Barwick ...................... 604/104 |
| 5,059,169 A | 10/1991 | Zilber ............................ 604/8 |
| 5,061,275 A | 10/1991 | Wallsten et al. ................ 623/1 |
| 5,078,720 A | 1/1992 | Burton et al. ............... 606/108 |
| 5,087,252 A | 2/1992 | Denard ........................ 604/346 |
| 5,116,309 A | 5/1992 | Coll ................................ 604/8 |
| 5,122,154 A | 6/1992 | Rhodes |
| 5,147,370 A | 9/1992 | McNamara et al. ......... 606/108 |
| 5,160,341 A | 11/1992 | Brenneman et al. |
| 5,167,614 A | 12/1992 | Tessmann et al. ............. 604/8 |
| 5,176,625 A | 1/1993 | Brisson |
| 5,176,626 A | 1/1993 | Soehendra |
| 5,183,085 A | 2/1993 | Timmermans |
| 5,195,989 A | 3/1993 | Euteneuer |
| 5,220,927 A | 6/1993 | Astrahan et al. ............. 128/785 |
| 5,221,253 A | 6/1993 | Coll ................................ 604/8 |
| 5,222,971 A | 6/1993 | Willard et al. |
| 5,224,953 A | 7/1993 | Morgentaler ................ 606/192 |
| 5,234,456 A | 8/1993 | Silvestrini |
| 5,246,445 A | 9/1993 | Yachia et al. ............... 606/108 |
| 5,258,020 A | 11/1993 | Froix |
| 5,269,802 A | 12/1993 | Garber |
| 5,282,784 A | 2/1994 | Willard |
| 5,282,823 A | 2/1994 | Schwartz et al. |
| 5,286,254 A | 2/1994 | Shapland et al. |
| 5,292,315 A | 3/1994 | Euteneuer |
| 5,300,022 A | 4/1994 | Klapper et al. ................ 604/35 |
| 5,304,121 A | 4/1994 | Sahatjian |
| 5,316,016 A | 5/1994 | Adams et al. |
| 5,322,501 A | 6/1994 | Mahmud-Durrani |
| 5,342,348 A | 8/1994 | Kaplan |
| 5,344,395 A | 9/1994 | Whalen et al. |
| 5,346,467 A | 9/1994 | Coll ................................ 604/8 |
| 5,352,198 A | 10/1994 | Goldenberg et al. .......... 604/95 |
| 5,354,263 A | 10/1994 | Coll ................................ 604/8 |
| 5,354,309 A | 10/1994 | Schnepp-Pesch et al. ... 606/198 |
| 5,356,423 A | 10/1994 | Tihon et al. .................. 606/194 |
| 5,364,340 A | 11/1994 | Coll ................................ 604/8 |
| 5,372,600 A | 12/1994 | Beyar et al. .................. 606/108 |
| 5,383,928 A | 1/1995 | Scott et al. ...................... 623/1 |
| 5,391,196 A | 2/1995 | Devonec ........................ 607/96 |
| 5,419,760 A | 5/1995 | Narciso, Jr. |
| 5,421,955 A | 6/1995 | Lau et al. |
| 5,429,634 A | 7/1995 | Narciso, Jr. |
| 5,441,515 A | 8/1995 | Khosravi et al. |
| 5,441,516 A | 8/1995 | Wang et al. |
| 5,464,650 A | 11/1995 | Berg et al. |
| 5,496,277 A | 3/1996 | Termin et al. |
| 5,499,994 A | 3/1996 | Tihon et al. |
| 5,514,176 A | 5/1996 | Bosley, Jr. ....................... 623/1 |
| 5,514,178 A | 5/1996 | Torchio ......................... 623/12 |
| 5,514,669 A | 5/1996 | Selman |
| 5,520,697 A | 5/1996 | Lindenberg et al. ......... 606/108 |
| 5,536,242 A | 7/1996 | Willard et al. |
| 5,540,713 A | 7/1996 | Schnepp-Pesch et al. ... 606/198 |
| 5,545,208 A | 8/1996 | Wolff et al. |
| 5,549,559 A | 8/1996 | Eshel |
| 5,554,181 A | 9/1996 | Das |
| 5,556,413 A | 9/1996 | Lam |
| 5,562,622 A | 10/1996 | Tihon |
| 5,584,872 A | 12/1996 | LaFontaine et al. |
| 5,588,965 A | 12/1996 | Burton et al. |
| 5,593,403 A | 1/1997 | Buscemi |
| 5,599,306 A | 2/1997 | Klein et al. |
| 5,601,591 A | 2/1997 | Edwards et al. |
| 5,609,583 A | 3/1997 | Hakki et al. ................. 604/282 |
| 5,609,629 A | 3/1997 | Fearnot et al. |
| 5,618,299 A | 4/1997 | Khosravi et al. |
| 5,626,562 A | 5/1997 | Castro |
| 5,667,486 A | 9/1997 | Mikulich et al. ............... 604/8 |
| 5,667,490 A | 9/1997 | Keith et al. |
| 5,674,241 A | 10/1997 | Bley et al. .................... 606/198 |
| 5,676,693 A | 10/1997 | LaFontaine |
| 5,702,361 A | 12/1997 | Evans et al. |
| 5,702,419 A | 12/1997 | Berry et al. |
| 5,707,386 A | 1/1998 | Schnepp-Pesch et al. ... 606/194 |
| 5,723,003 A | 3/1998 | Winston et al. |
| 5,725,549 A | 3/1998 | Lam |
| 5,733,303 A | 3/1998 | Israel et al. |
| 5,738,654 A | 4/1998 | Tihon |
| 5,766,209 A | 6/1998 | Devonec .......................... 604/8 |
| 5,766,238 A | 6/1998 | Lau et al. |
| 5,772,668 A | 6/1998 | Summers et al. |
| 5,776,142 A | 7/1998 | Gunderson |
| 5,776,161 A | 7/1998 | Globerman .................. 606/194 |
| 5,782,838 A | 7/1998 | Beyar et al. |
| 5,792,400 A | 8/1998 | Talja et al. ................... 264/103 |
| 5,797,952 A | 8/1998 | Klein |
| 5,817,102 A | 10/1998 | Johnson et al. ............. 606/108 |
| 5,824,037 A | 10/1998 | Fogarty et al. |
| 5,824,038 A | 10/1998 | Wall |
| 5,830,179 A | 11/1998 | Mikus et al. ................... 604/49 |
| 5,833,707 A | 11/1998 | McIntyre et al. ............. 606/198 |
| 5,843,103 A | 12/1998 | Wulfman |
| 5,860,999 A | 1/1999 | Schnepp-Pesch et al. ... 606/194 |
| 5,865,815 A | 2/1999 | Tihon ........................... 604/280 |
| 5,876,417 A | 3/1999 | Devonec et al. ............. 606/192 |
| 5,876,445 A | 3/1999 | Andersen et al. |
| 5,888,201 A | 3/1999 | Stinson et al. |
| 5,902,328 A | 5/1999 | LaFontaine et al. |
| 5,911,752 A | 6/1999 | Dustrude et al. |
| 5,916,195 A | 6/1999 | Eshel et al. ..................... 604/96 |
| 5,916,227 A | 6/1999 | Keith et al. |
| 5,928,208 A | 7/1999 | Chu et al. ..................... 604/280 |
| 5,928,217 A | 7/1999 | Mikus et al. ................. 604/530 |
| 5,938,670 A | 8/1999 | Keith et al. |
| 5,957,929 A | 9/1999 | Brenneman |
| 5,964,732 A | 10/1999 | Willard |
| 5,964,744 A | 10/1999 | Balbierz et al. |
| 5,964,771 A | 10/1999 | Beyar et al. .................. 606/108 |
| 5,976,165 A | 11/1999 | Ball et al. |
| 5,980,550 A | 11/1999 | Eder et al. |
| 6,001,117 A | 12/1999 | Huxel et al. |
| 6,004,328 A | 12/1999 | Solar |
| 6,017,977 A | 1/2000 | Evans et al. |
| 6,019,779 A | 2/2000 | Thorud et al. |
| 6,022,312 A | 2/2000 | Chaussy et al. ............... 600/29 |
| 6,023,638 A | 2/2000 | Swanson |
| 6,024,763 A | 2/2000 | Lenker et al. |
| 6,033,413 A | 3/2000 | Mikus et al. ................. 606/108 |
| 6,042,606 A | 3/2000 | Frantzen |
| 6,047,218 A | 4/2000 | Whayne et al. |
| 6,050,949 A | 4/2000 | White et al. |
| 6,053,900 A | 4/2000 | Brown et al. |
| 6,066,167 A | 5/2000 | Lau et al. |
| 6,066,168 A | 5/2000 | Lau et al. |
| 6,090,103 A | 7/2000 | Hakky et al. |
| 6,090,115 A | 7/2000 | Beyar et al. |
| 6,113,594 A | 9/2000 | Savage |
| 6,113,597 A | 9/2000 | Eggers et al. |
| 6,119,697 A | 9/2000 | Engel et al. |
| 6,126,667 A | 10/2000 | Barry et al. |

| | | | | | |
|---|---|---|---|---|---|
| 6,132,460 A | 10/2000 | Thompson | 2003/0045924 A1 | 3/2003 | Datta et al. |

FOREIGN PATENT DOCUMENTS

| | | |
|---|---|---|
| 6,132,461 A | 10/2000 | Thompson |
| 6,139,536 A | 10/2000 | Mikus et al. ............... 604/500 |
| 6,146,416 A | 11/2000 | Andersen et al. |
| 6,152,919 A | 11/2000 | Hakky |
| 6,156,064 A | 12/2000 | Chouinard |
| 6,162,215 A | 12/2000 | Feng |
| 6,162,231 A | 12/2000 | Mikus et al. |
| 6,165,210 A | 12/2000 | Lau et al. |
| 6,174,305 B1 | 1/2001 | Mikus et al. |
| 6,176,875 B1 | 1/2001 | Lenker et al. |
| 6,179,868 B1 | 1/2001 | Burpee et al. |
| 6,187,015 B1 | 2/2001 | Brenneman |
| 6,214,037 B1 | 4/2001 | Mitchell et al. |
| 6,221,081 B1 | 4/2001 | Mikus et al. |
| 6,238,430 B1 | 5/2001 | Klumb et al. |
| 6,254,628 B1 | 7/2001 | Wallace et al. |
| 6,334,866 B1 | 1/2002 | Wall |
| 6,355,061 B1 | 3/2002 | Quiachon et al. |
| 6,371,979 B1 | 4/2002 | Beyar et al. |
| 6,451,025 B1 | 9/2002 | Jervis |
| 6,494,879 B2 | 12/2002 | Lennox et al. |
| 6,494,908 B1 | 12/2002 | Huxel et al. |
| 2002/0107540 A1 | 8/2002 | Whalen et al. |
| 2002/0177904 A1 | 11/2002 | Huxel et al. |
| 2003/0040803 A1 | 2/2003 | Rioux et al. |

| | | |
|---|---|---|
| EP | 0 341 988 | 11/1989 |
| EP | 0 543 309 A1 | 11/1992 |
| EP | 0 935 977 A3 | 8/1999 |
| WO | WO 80/01460 | 7/1980 |
| WO | WO 89/03232 | 4/1989 |
| WO | WO 91/16005 | 10/1991 |
| WO | WO 96/23449 | 8/1996 |
| WO | 99/23952 | 5/1999 |
| WO | WO 00/15130 | 3/2000 |
| WO | WO 00/16005 | 3/2000 |
| WO | WO 00/18907 | 4/2000 |
| WO | WO 00/19926 | 4/2000 |
| WO | WO 00/21462 | 4/2000 |
| WO | WO 00/51521 | 9/2000 |
| WO | WO 00/56247 | 9/2000 |
| WO | WO 00/59558 | 10/2000 |
| WO | WO 00/69367 | 11/2000 |
| WO | WO 00/69498 | 11/2000 |
| WO | WO 00/76425 | 12/2000 |
| WO | WO 01/10345 | 2/2001 |
| WO | WO 01/56629 | 8/2001 |
| WO | WO 02/005841 | 8/2002 |

OTHER PUBLICATIONS

PCT International Search Report for PCT/US02/14895.

DRAINING BODILY FLUIDS WITH A STENT

CROSS-REFERENCE TO RELATED APPLICATION

This application is a divisional application of, and claims priority to, U.S. patent application Ser. No. 09/862,270, filed May 22, 2001, now U.S. Pat. No. 6,981,964, the disclosure of which is incorporated herein by reference in its entirety.

TECHNICAL FIELD

This invention generally relates to stents and draining bodily fluids using stents.

BACKGROUND INFORMATION

Bladder outlet obstruction is a urological disorder. In men, this urological disorder can be caused by an enlarged prostate that constricts the prostatic urethra. The prostatic urethra is a section of the urethra that passes through the prostate. Bladder outlet obstruction is associated with a plurality of undesirable symptoms such as difficulties urinating and an increased desire to urinate.

To eliminate these symptoms, medical devices that attempt to maintain an open passageway through the prostatic urethra have been developed. One of the medical devices developed for this purpose is a Foley catheter. The Foley catheter is a tube that extends from the patient's bladder to a collection bag located outside of the patient's body. The Foley catheter provides constant drainage, but it does not allow the patient to control his voiding function.

Some indwelling prostatic stents seek to allow the patient to control their voiding function while also retaining the prostatic urethra open. For example, U.S. Pat. No. 5,766,209 describes a prosthesis that contains two tubular elements that are intended to be arranged on either side of the patient's external sphincter, and a connector that is intended to be held in the orifice of the external sphincter.

SUMMARY OF THE INVENTION

The invention generally relates to draining fluid from the bladder of a male patient with a stent. Devices and methods according to the invention are typically used in the treatment for male patients suffering from bladder outlet obstruction to address and relieve urinary retention. It is an object of the invention to maintain the prostatic urethra open and able to pass fluids from the bladder while also allowing normal operation of the patient's external sphincter such that the patient has control over the retention and discharge of urine (and/or other fluids) from the bladder. It is another object of the invention to resist migration of a device placed within the patient's urinary system, and also to prevent or reduce the attraction of blood clots (and/or other debris) when the device is placed and used within the patient.

It is noted initially that the directional terms proximal and distal require a point of reference. As used herein, the point of reference is from the perspective of the body of the patient. Therefore, the term proximal refers to a direction that points into the body of the patient, whereas the term distal refers to a direction that points out of the patient's body.

In general, in one aspect, the invention relates to a prostatic stent. The prostatic stent comprises a first segment including a multi-winged malecot, a second segment, and a connecting member disposed between the first and second segments. The first segment includes a proximal portion, a distal end, and a lumen extending within the first segment. The proximal portion of the first segment includes both the multi-winged malecot and at least one opening in communication with the lumen for receiving fluid from the bladder of the patient. When the prostatic stent is properly positioned within the body of the patient, the first segment is located on the proximal side of the external sphincter with the multi-winged malecot located substantially within the bladder of the patient to inhibit the distal migration (down out of the bladder and out of the patient's urinary system) of the prostatic stent, and the distal end terminating on the proximal side of the external sphincter. To prevent the distal migration of the prostatic stent, the multi-winged malecot includes two or more wings that are collapsible to allow for the passage of the prostatic stent into and through the urethra of the patient and expandable to hold the remainder of the prostatic stent within the urethra of the patient when located in the bladder. The multi-winged malecot may be biased in an expanded configuration such that the multi-winged malecot will return to the expanded configuration in the absence of external forces acting upon the multi-winged malecot.

The second segment of the prostatic stent includes a proximal end, a distal end, and a lumen extending within the second segment. When the prostatic stent is placed within the body of the patient, the second segment is located on the distal side of the external sphincter with the proximal end terminating on the distal side of the external sphincter. The second segment prevents the proximal migration (up into the bladder) of the prostatic stent.

The connecting member of the prostatic stent couples the first segment to the second segment, and is therefore located within the patient's external sphincter when the prostatic stent is properly positioned. The connecting member is sized to pass through the patient's external sphincter without affecting normal operation of the external sphincter and thus allows the patient to maintain normal control of voiding function. The connecting member couples the first and second segments together with a smooth transition at the distal end of the first segment and the proximal end of the second segment. The smooth transition between the first segment and the connecting member and the second segment and the connecting member inhibits the collection of blood and other bodily materials at the distal and proximal ends of the first and second segments when the prostatic stent is placed within the patient's body.

Embodiments of this aspect of the invention can include the following features. The first segment can include a reinforcing element to prevent kinking or buckling of the first segment, which can lead to obstruction of fluids through the prostatic urethra. The reinforcing element can be a wire coil, a wire mesh tube, or another element that increases the radial strength of the first segment. The connecting member can be made from a wire including a first end and a second end. The first and second ends of the wire may be embedded within the first and second segments, respectively so as to produce a smooth transition at the distal and proximal ends. To promote a comfortable and prompt insertion of the prostatic stent, the proximal portion of the first segment can include a curved proximal tip. During insertion the curved proximal tip can provide comfort to the patient when a medical professional who is inserting the prostatic stent is navigating around a natural bend in the patient's urethra. The prostatic stent can also include an elongated member that extends from the second segment through the urethra and out of the meatus. At least a portion of the elongated member may be embedded within the second segment so as not to produce hanging ends, rough discontinuities and/or other viable surfaces for the collection of blood clots and/or other bodily materials. The elongated member is a useful tool for removing the prostatic stent from the patient's body. To remove the prostatic stent, the medical professional simply pulls on the elongated body member.

In general, in another aspect, the invention features a prostatic stent that includes a first segment having an inflatable balloon for inhibiting the distal migration of the prostatic stent, a second segment, and a connecting member disposed between the first and second segments. The first segment further includes a proximal portion, a distal end, and a lumen extending within the first segment. The proximal portion of the first segment contains both the inflatable balloon and at least one opening in communication with the lumen for receiving fluid from the bladder of the patient. To fill the inflatable balloon, the inflatable balloon is in communication with an inflation channel extending between the inflatable balloon and a valve located on the distal end of the first segment. The valve controls fluid flow in and out of the inflation channel. When the prostatic stent is properly positioned within the body of the patient, the first segment is located on the proximal side of the external sphincter with the inflatable balloon located substantially within the bladder of the patient to inhibit the distal migration of the prostatic stent, and the distal end terminating on the proximal side of the external sphincter. Once the inflatable balloon is located within the patient's bladder, the inflatable balloon is filled with a fluid, such as saline or air, and thereby acts as an anchor to keep the prostatic stent positioned within the urethra.

The second segment of the prostatic stent includes a proximal end, a distal end, and a lumen extending within the second segment. When the prostatic stent is placed within the body of the patient, the second segment is located on the distal side of the external sphincter with the proximal end terminating on the distal side of the external sphincter. The second segment prevents the proximal migration of the prostatic stent.

The connecting member of the prostatic stent couples the first segment to the second segment, and is therefore located within the patient's external sphincter when the prostatic stent is properly positioned. The connecting member is sized to pass through the patient's external sphincter without affecting normal operation of the external sphincter and thus allows the patient to maintain normal control of voiding function. The connecting member couples the first and second segments together with a smooth transition at the distal end of the first segment and the proximal end of the second segment. The smooth transition between the first segment and the connecting member and the second segment and the connecting member inhibits the collection of blood and other bodily materials at the distal and proximal ends of the first and second segments when the prostatic stent is placed within the patient's body.

Embodiments of this aspect of the invention can include the following features. The first segment can include a reinforcing element to prevent kinking or buckling of the first segment, which can lead to obstruction of fluids through the prostatic urethra. The reinforcing element can be a wire coil, a wire mesh tube, or another element that increases the radial strength of the first segment. In one embodiment, the connecting member can be made from a wire including a first end and a second end. The first and second ends of the wire may be embedded within the first and second segments, respectively so as to produce a smooth transition at the distal and proximal ends. In another embodiment, the connecting member can be made from the same material as the first and second segments and can be integrally connected to the first and second segments. Another feature is a curved proximal tip that promotes a comfortable and prompt insertion of the prostatic stent. During insertion the curved proximal tip can provide comfort to the patient when a medical professional who is inserting the prostatic stent is navigating around a natural bend in the patient's urethra. The prostatic stent can also include an elongated member that extends from the second segment through the urethra and out of the meatus. At least a portion of the elongated member may be embedded within the second segment so as not to produce hanging ends, rough discontinuities and/or other viable surfaces for the collection of blood clots and/or other bodily materials. The elongated member is a useful tool for removing the prostatic stent from the patient's body. To remove the prostatic stent, the medical professional simply pulls on the elongated body member.

In general, in another aspect, the invention features a prostatic stent that includes a first segment having an inflatable balloon for inhibiting the distal migration of the prostatic stent and a reinforcing element for preventing kinking, a second segment, a connecting member disposed between the first and second segments, and an inflation channel extending between the inflatable balloon and a valve located on the second segment. The first segment further includes a proximal portion, a distal end, and a lumen extending within the first segment. The proximal portion of the first segment contains both the inflatable balloon and at least one opening in communication with the lumen for receiving fluid from the bladder of the patient. When the prostatic stent is properly positioned within the body of the patient, the first segment is located on the proximal side of the external sphincter with the inflatable balloon located substantially within the bladder of the patient to inhibit the distal migration of the prostatic stent, and the distal end terminating on the proximal side of the external sphincter. Once the inflatable balloon is located within the patient's bladder, the inflatable balloon is filled with a fluid, such as saline or air, and thereby acts as an anchor to prevent distal migration of the prostatic stent.

The second segment of the prostatic stent includes a proximal end, a distal end, and a lumen extending within the second segment. The valve located on the distal end of the second segment controls fluid flow in and out of the inflation channel. When the prostatic stent is placed within the body of the patient, the second segment is located on the distal side of the external sphincter with the proximal end terminating on the distal side of the external sphincter. The second segment prevents the proximal migration of the prostatic stent.

The connecting member of the prostatic stent is sized to pass through the patient's external sphincter without affecting normal operation of the external sphincter and thus allows the patient to maintain normal control of voiding function. The connecting member couples the first and second segments together with a smooth transition at the distal end of the first segment and the proximal end of the second segment. The smooth transition between the first segment and the connecting member and the second segment and the connecting member inhibits the collection of blood and other bodily materials at the distal and proximal ends of the first and second segments when the prostatic stent is placed within the patient's body.

Embodiments of this aspect of the invention can include the following features. The reinforcing element can be a wire coil, a wire mesh tube, or another element that increases the radial strength of the first segment. The connecting member can be made from the same material as the first and second segments and can be integrally connected to the first and second segments. To promote a comfortable and prompt insertion of the prostatic stent, the proximal portion of the first segment can include a curved proximal tip. The curved proximal tip can provide comfort to the patient during insertion when a medical professional who is inserting is navigating the prostatic stent around a natural bend in the patient's urethra. The prostatic stent can also feature an elongated member that extends from the second segment through the urethra. At least a portion of the elongated member may be embedded within the second segment so as not to produce handing ends, rough discontinuities and/or other viable surfaces for the collection of blood clots and/or other bodily materials. The elongated member is a useful tool for removing the prostatic stent from the patient's body. To remove the prostatic stent, the medical professional simply pulls on the elongated body member.

In another aspect, the invention relates to a method of positioning a prostatic stent within the urinary system of a patient. The prostatic stent that is to be inserted includes a first segment including a multi-winged malecot, a second segment, and a connecting member disposed between the first and second segments. Both the first and second segments are tubular members containing lumens to convey fluids from the bladder. When properly positioned within the patient's body, the first segment is located on the proximal side of the external sphincter with a proximal portion including the multi-winged malecot locatable within the bladder, the second segment is located on the distal side of the external sphincter, and the connecting member extends through the external sphincter but does not interfere with the normal operation of the external sphincter.

A medical professional such as a physician performing the method uses a stylet for advancing the prostatic stent through the patient's urethra. The stylet has a proximal end and a distal end. The stylet should be long enough such that the proximal end of the stylet can contact the proximal portion of the first segment while the distal end of the stylet remains outside of the patient's body when the prostatic stent is properly positioned within the urinary system of the patient. The width of the stylet should be less than the width of the first and second segments so that the stylet can be placed within the lumens of the first and second segments. To connect the stylet and prostatic stent together, the medical professional passes the stylet through the lumens of the second and first segments of the prostatic stent.

Before the medical professional inserts the prostatic stent, he or she places the multi-winged malecot in an insertion configuration (for example, collapses the multi-winged malecot by proximally extending the proximal portion of the first segment). The medical professional then inserts the proximal portion of the prostatic stent into the patient's urethra at the meatus. The medical professional advances the prostatic stent through the urethra until the first segment is located substantially within the prostatic urethra with the proximal portion located within the bladder and the distal end terminating on the proximal side of the external sphincter. At this point, the second segment is located on the distal side of the external sphincter, and the connecting member should be positioned within the external sphincter connecting the first segment to the second segment. Once located in the bladder, the medical professional expands the multi-winged malecot, thereby anchoring the prostatic stent within the patient's urinary system and preventing distal migration of the prostatic stent. The second segment, which is located on the distal side of the external sphincter, prevents proximal migration of the prostatic stent. After confirming proper positioning of the prostatic stent, the medical professional removes the stylet completely from the lumens of the first and second segments and from the patient's urethra, thereby leaving the prostatic stent positioned within the patient's urinary system. The patient's external sphincter is then able to contract around the connecting member whereby allowing the patient to control the retention and discharge or urine from their bladder. The prostatic stent remains within the patient's urethra anchored in position by the multi-winged malecot and the second segment and maintains an open passageway for conveying fluids from the patient's bladder. At some later time, the prostatic stent may be removed from the patient's body by pulling on an elongated member that is attached to the prostatic stent.

In another aspect, the invention relates to a method of positioning a prostatic stent within the urinary system of a patient. The prostatic stent that is to be inserted includes a first segment including a inflatable balloon, a second segment, and a connecting member disposed between the first and second segments. Both the first and second segments are tubular members containing lumens to convey fluids from the bladder. When properly positioned within the patient's body, the first segment is located on the proximal side of the external sphincter with a proximal portion including the multi-winged malecot locatable within the bladder, the second segment is located on the distal side of the external sphincter, and the connecting member extends through the external sphincter but does not interfere with the normal operation of the external sphincter.

A medical professional such as a physician performing the method uses a stylet for advancing the prostatic stent through the patient's urethra. The stylet has a proximal end and a distal end. The stylet should be long enough such that the proximal end of the stylet can contact the proximal portion of the first segment while the distal end of the stylet remains outside of the patient's body when the prostatic stent is properly positioned within the urinary system of the patient. The width of the stylet should be less than the width of the first and second segments so that the stylet can be placed within the lumens of the first and second segments. To connect the stylet and prostatic stent together, the medical professional passes the stylet through the lumens of the second and first segments of the prostatic stent.

Before the medical professional inserts the prostatic stent, he or she places the inflatable balloon in an insertion configuration (for example, the inflatable balloon is unfilled). To fill the inflatable balloon with fluid in vivo the medical professional uses an inflation segment and a syringe. The inflation segment has a first end, a second end, and a lumen extending within the inflation segment. Prior to insertion, the first end is connected the syringe and the second end is connected to the inflation channel. The medical professional then inserts the proximal portion of the prostatic stent into the patient's urethra at the meatus. The medical professional advances the prostatic stent through the urethra until the first segment is located substantially within the prostatic urethra with the proximal portion located within the bladder and the distal end terminating on the proximal side of the external sphincter. At this point, the second segment is located on the distal side of the external sphincter, and the connecting member should be positioned within the external sphincter connecting the first segment to the second segment. Once located in the bladder, the medical professional fills the inflatable balloon with fluid by activating the syringe to force fluid from the syringe through the lumen of the inflation segment, to the inflation channel, and finally to the inflatable balloon. The filled inflatable balloon anchors the prostatic stent within the patient's urinary system and prevents distal migration of the prostatic stent. The second segment, which is located on the distal side of the external sphincter, prevents proximal migration of the prostatic stent. After confirming proper positioning of the prostatic stent, the medical professional disconnects the inflation segment from the prostatic stent and removes both the stylet and the inflation segment completely from the patient's urethra, thereby leaving the prostatic stent positioned within the patient's urinary system. The patient's external sphincter is then able to contract around the connecting member whereby allowing the patient to control the retention and discharge or urine from their bladder. The prostatic stent remains within the patient's urethra anchored in position by the inflatable balloon and the second segment and maintains an open passageway for conveying fluids from the patient's bladder. At some later time, the prostatic stent may be removed from the patient's body by first deflating the inflatable balloon and then pulling on an elongated member that is attached to the prostatic stent.

The foregoing and other objects, aspects, features and advantages of the invention will become more apparent from the following description including drawings and from the claims.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention.

FIG. 11 is a cross-sectional view of the prostatic stent taken along line NN in FIG. 11.

DESCRIPTION

The invention generally relates to relieving urinary retention. The invention provides devices and methods for assisting urinary release in a male patient suffering from bladder outlet obstruction while allowing normal operation of the patient's external sphincter such that the patient has control over bladder voiding.

Some men, especially men over fifty years of age, experience urinary retention caused by an enlarged prostate. The prostate is a chestnut shaped organ that surrounds the urethra in a man's urinary system. When it becomes enlarged due to disease or changes in male hormone production, the prostate can constrict the urethra resulting in bladder outlet obstruction. The medical condition described above is generally referred to as benign prostatic hyperplasia (BPH). In addition to the obstruction caused by the enlarged prostate, blood clots or other debris collecting in the constricted urethra may further obstruct the urethra of a patient suffering from BPH. One of the objects of the present invention is to maintain an open passageway clear of debris from the patient's bladder through the urethra while preserving the patient's normal control of voiding function by allowing the external sphincter to open and close normally and under patient control.

Figure 1A:
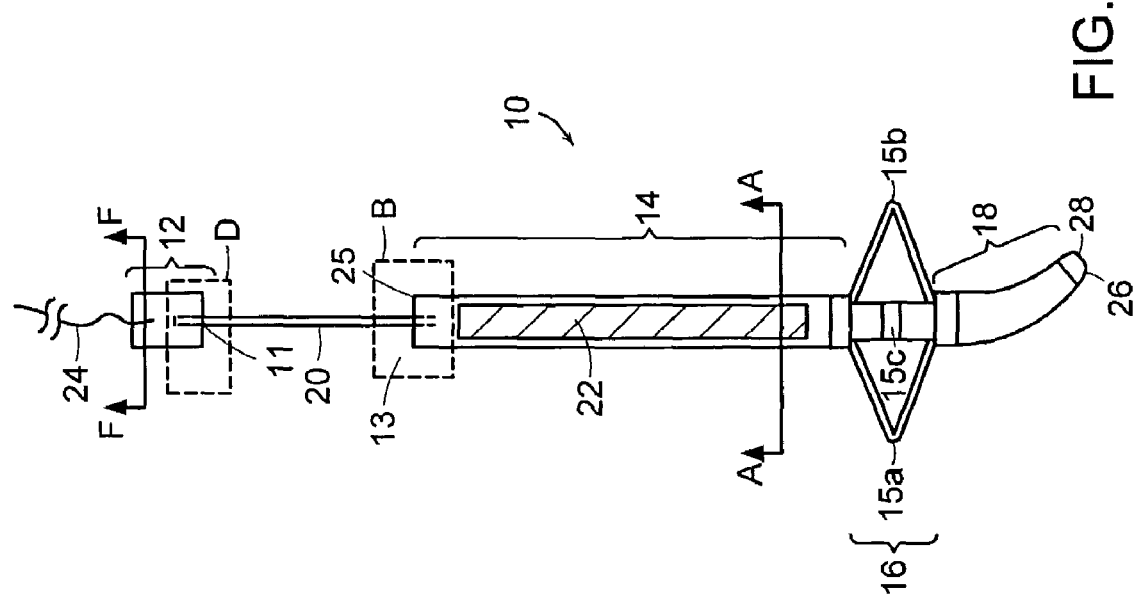
FIG. 1A is a side view of one embodiment of a prostatic stent according to the present invention.

Referring to FIG. 1A, a prostatic stent 10 of the invention is made from one or more biocompatible materials such as silicone or stainless steel. The prostatic stent 10 comprises a bulbar segment 12, a prostatic segment 14, a multi-winged malecot 16, and a connecting segment 20. In the disclosed embodiment, the bulbar segment 12 and the prostatic segment 14 are both cylindrical tubular elements that are sufficiently flexible to conform to the shape of the urethra for insertion ease while simultaneously are also sufficiently rigid to maintain an open passageway through the urethra. The segments 12, 14 could have cross-sectional shapes other than circular, such as elliptical or even rectangular, square, or triangular, for example. In the disclosed embodiment shown in FIG. 1A, the prostatic stent 10 further includes a proximal tip 18 extending proximally from the multi-winged malecot 16. The proximal tip 18 has a proximal end 26 and can be straight or curved as shown in FIG. 1A. The proximal tip 18 further includes an opening 28 sized to receive a guide wire.

When the prostatic stent 10 is properly positioned within a male patient's urinary system, the multi-winged malecot 16 is located within the bladder near the bladder opening, the prostatic segment 14 is located substantially within the prostatic urethra (the section of the urethra that is surrounded by the patient's prostate) with a distal end 25 of the prostatic segment 14 terminating just prior to the proximal side of the patient's external sphincter, and the bulbar segment 12 is located on the distal side of the external sphincter. The connecting segment 20 is sized to extend through the external sphincter to attach the bulbar segment 12 to the prostatic segment 14 while not interfering with the normal operation of the external sphincter. The connecting segment 20 in the embodiment shown in FIG. 1A is a wire. The wire is made from stainless steel and is coated with a thin layer of silicone. One end of the wire is embedded in the bulbar segment 12 while the other end is embedded within the prostatic segment 14. The connecting segment 20 can also be made from other biocompatible metals such as titanium, a suture, or a strip of a biocompatible polymer or other material that is thin enough to extend through the external sphincter without negatively affecting its normal operation and that is strong enough to couple together the bulbar and prostatic segments 12, 14. Each of the ends of the connecting segment 20 is attached to the respective bulbar and the prostatic segments 12, 14 in such a way as to form a smooth transition having no rough discontinuities or edges that would collect blood and/or other bodily material.

Figure 1B:
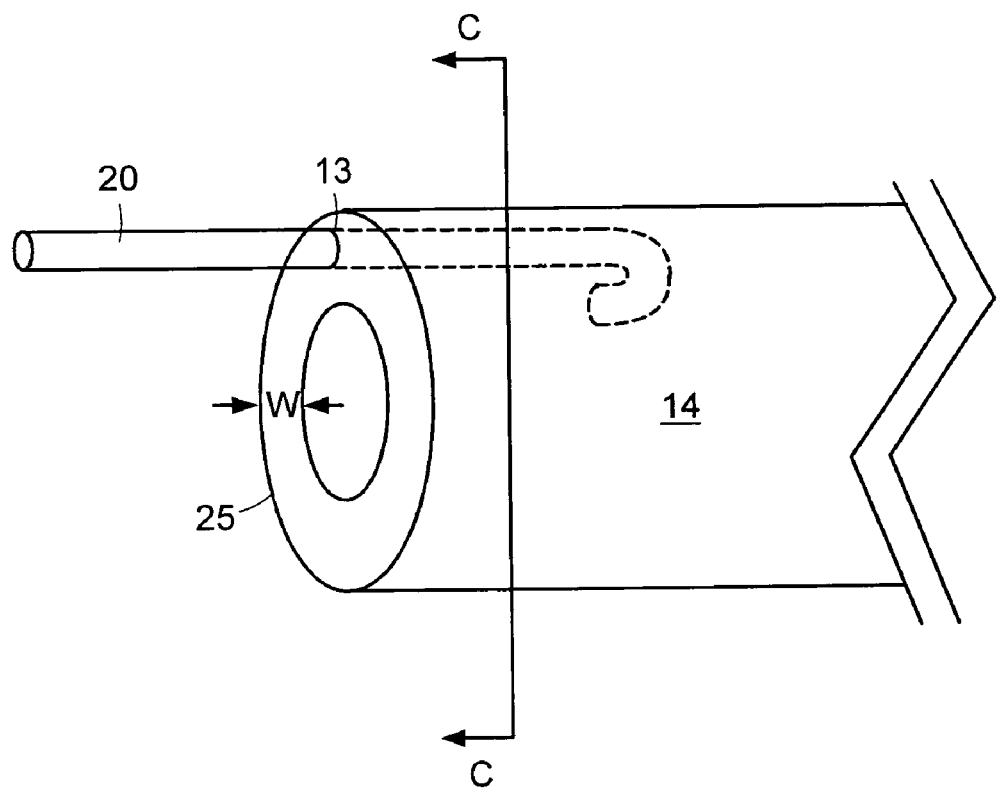
FIG. 1B shows an enlarged perspective view of a section of the prostatic stent shown in FIG. 1A.
Figure 1C:
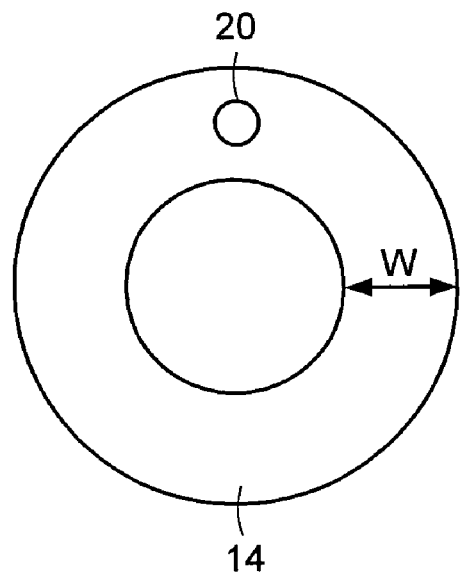
FIG. 1C shows an enlarged cross-sectional view taken along a line CC in FIG. 1B.
Figure 1E:
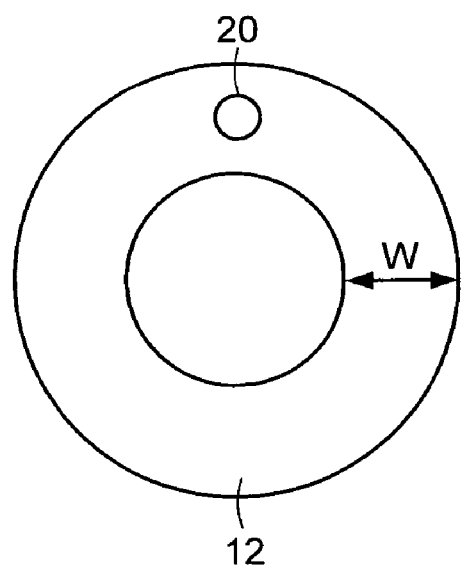
FIG. 1E shows an enlarged cross-sectional view taken along line EE in FIG. 1D.
Figure 1D:
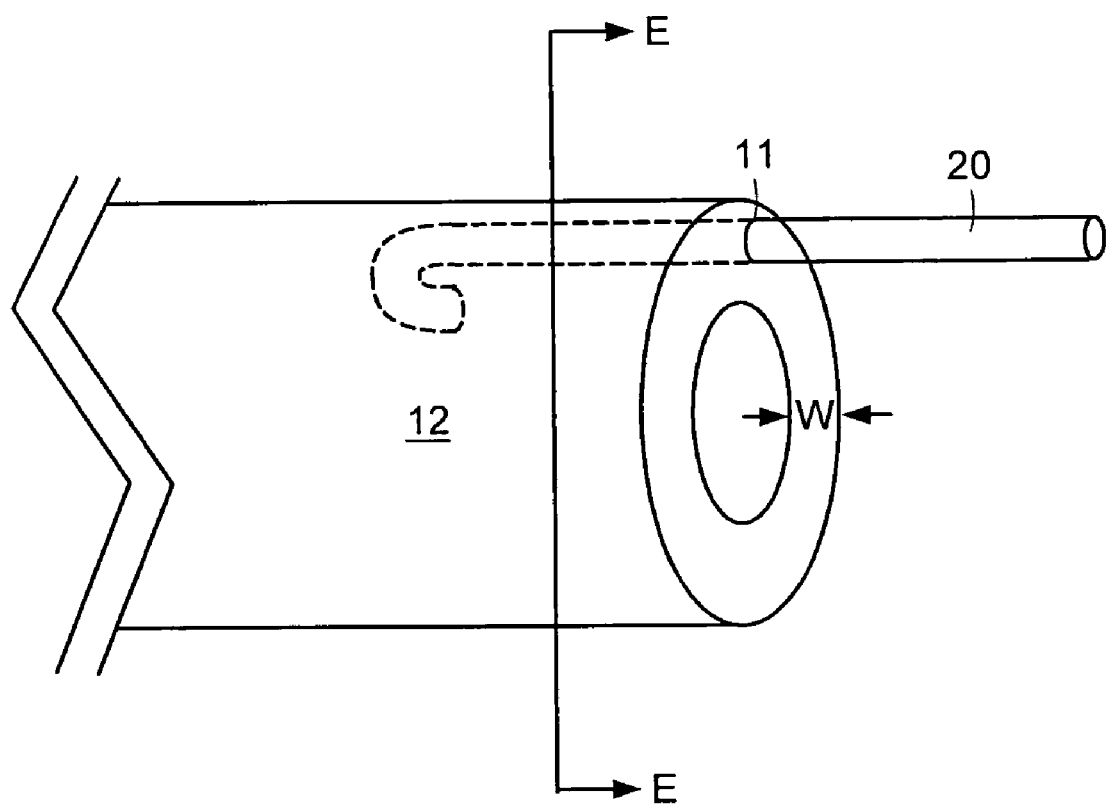
FIG. 1D shows an enlarged perspective view of another section of the prostatic stent shown in FIG. 1A.

The transitions 11, 13 from the segments 12, 14 to the connecting member 20 are smooth and thus prevent the collection of material and the formation of blood clots at the transitions 11, 13. FIGS. 1B and C show enlarged views of the transition 13 between the prostatic segment 14 and the connecting segment 20. FIG. 1B shows an enlarged perspective view of an area labeled B in FIG. 1A, and FIG. 1C shows an enlarged cross-sectional view taken along a line CC in FIG. 1b. A dimension labeled W defines the wall thickness of the segment. One of the ends of the connecting segment 20 is embedded within the wall of the prostatic segment 14 and the end does not puncture or penetrate through to the exterior wall of the prostatic segment 14. In the disclosed embodiment shown in FIG. 1B, the embedded end is bent into the shape of a hook, to provide a greater amount of contact surface area between the connecting segment 20 and the prostatic segment 14. The end terminates and is secured within the wall of the prostatic segment 14 by, for example, use of an adhesive or heat bonding the connecting segment 20 to the prostatic segment 14, thereby forming the transition 13 which is smooth (i.e., having no jagged surfaces or hanging ends on the exterior surface of the prostatic segment 14). The other transition 11 is also smooth. FIGS. 1D and 1E show enlarged perspective and cross-sectional views of the transition 11 between the bulbar 12 and connecting segments 12, 20. FIG. 1D shows an enlarged view of a section of the prostatic stent 10 which is labeled D in FIG. 1A. In FIG. 1D, the other end of the connecting segment 20 similarly is bent into a hook and embedded within the wall of the bulbar segment 12. FIG. 1E shows a cross-sectional view taken along line EE in FIG. 1D. This other end of the connecting segment 20 also is attached to the bulbar segment 12 in such a way as to not pierce the exterior wall of the bulbar segment 12, and the transition 11 thus also is smooth and free of jagged surfaces and/or hanging ends that would attract blood clots or other debris.

Figure 1H:
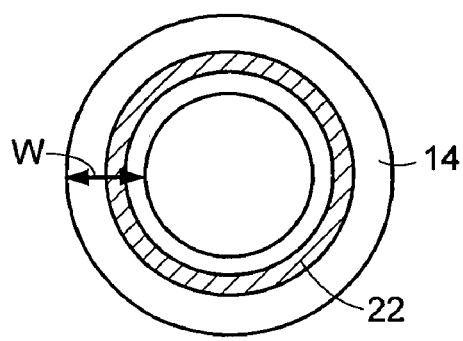
FIG. 1H is an enlarged cross-sectional view taken along line AA in FIG. 1A showing a prostatic stent with a reinforcing element embedded within the wall of a prostatic segment.
Figure 1I:
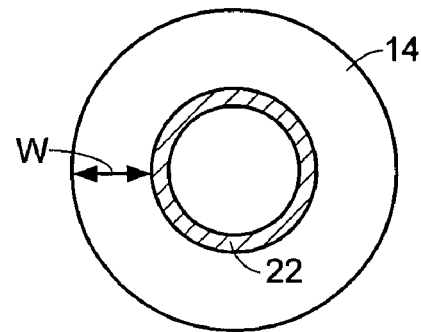
FIG. 1I is another enlarged cross-sectional view taken along line AA in FIG. 1A showing a prostatic stent with the reinforcing element lying against an interior wall of the prostatic segment.
Figure 1J:
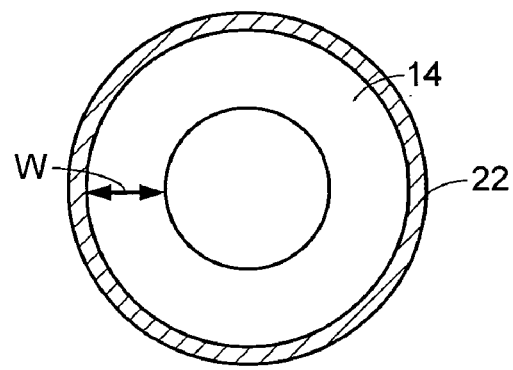
FIG. 1J is another enlarged cross-sectional view taken along line AA in FIG. 1A showing a prostatic stent with the reinforcing element lying against an exterior wall of the prostatic segment.
Figure 1F:
FIG. 1F is an enlarged perspective view of one embodiment of a reinforcing element.
Figure 1G:
FIG. 1G is an enlarged perspective view of another embodiment of a reinforcing element.

The prostatic stent 10, as shown in FIG. 1A, may further include a reinforcing element 22 such as a metallic coil (see FIG. 1F), wire mesh tube (see FIG. 1G), or other strength-adding member(s) such as, for example, multiple spaced bands of, for example, metal. The reinforcing element 22 can be made from any biocompatible material such as stainless steel and can be embedded within the wall of the prostatic segment 14 or can lie against either the interior wall that defines the lumen the prostatic segment 14 or the exterior wall that defines the outer diameter of the prostatic segment 14. Reinforcing elements that are exposed (i.e., lie against either the interior or exterior walls of the prostatic segment 14) may be coated with a thin layer of silicone or any other biocompatible polymer to prevent bodily materials, such as blood clots, from collecting on the reinforcing elements. FIGS. 1 H, I, and J are enlarged cross-sectional views taken along line AA in FIG. 1A, which shows the placement of the reinforcing element 22 within the prostatic sent 10. FIG. 1H shows the reinforcing element 22 embedded within the wall of the prostatic segment 14. FIG. 1I shows the reinforcing element 22 lying against the interior wall of the prostatic segment 14 and FIG. 1J shows the reinforcing element 22 lying against the exterior wall of the prostatic segment 14. The reinforcing element 22, regardless of its specific location, material, and structure, is designed to provide the prostatic stent 10 with at least three advantages. One advantage is that the reinforcing element 22 increases the tensile strength of the prostatic stent 10 thereby decreasing the possibility of obstruction due to a collapse of the prostatic segment's 14 lumen. Another advantage is that the presence of the reinforcing element 22 allows the wall thickness, W, of the prostatic segment 14 to be reduced. A decrease in wall thickness of the prostatic segment 14 allows for an increase in the inner diameter of the prostatic segment 14 (i.e., an increase in the lumen's size) which in turn allows for increased flow through the lumen of the prostatic segment 14. A third advantage is that the presence of the reinforcing element 22 increases the ability of the prostatic segment 14 to resist kinking or bending, which may results in obstruction of the prostatic stent 10.

Figure 1K:
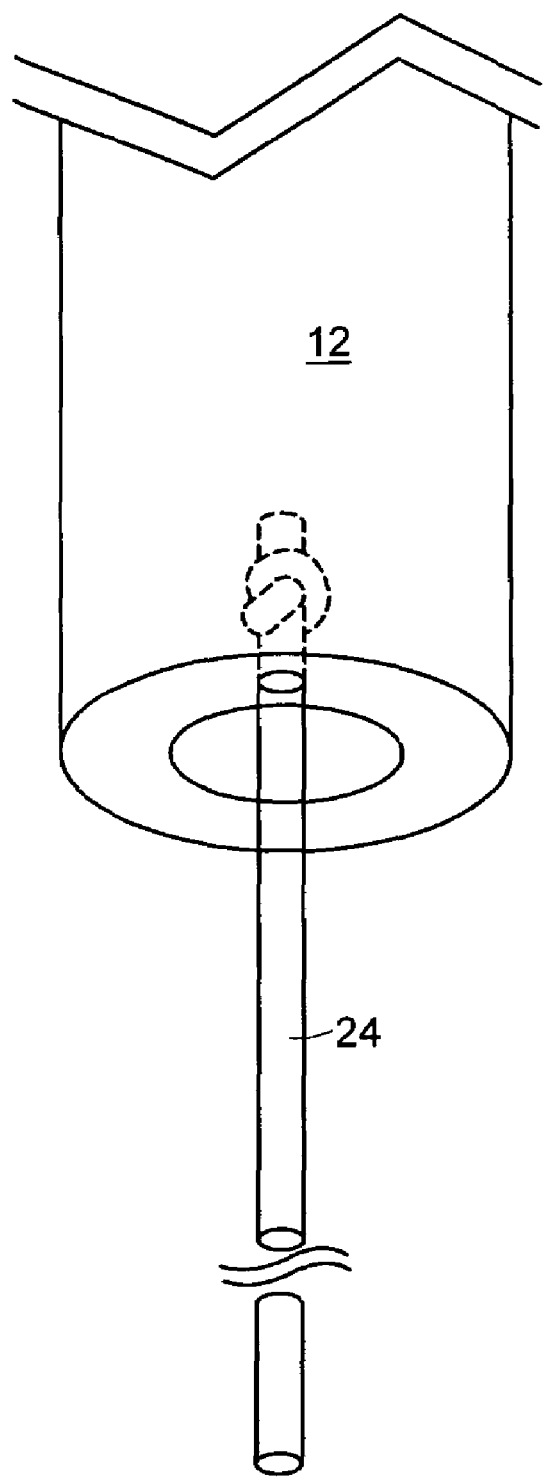
FIG. 1K is an enlarged perspective view of a removal segment connected to a bulbar segment.
Figure 1L:
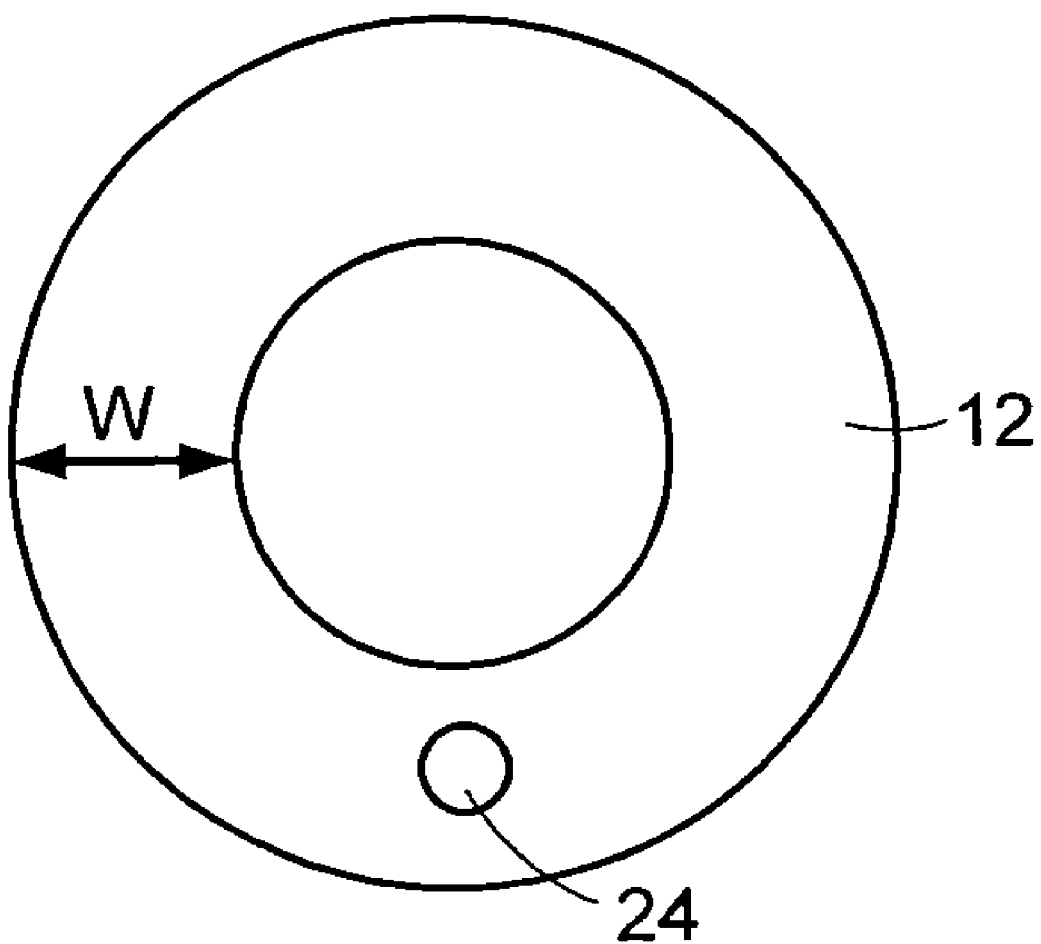
FIG. 1L is an enlarged cross-sectional view showing a connection between the removal segment and the bulbar segment.

Another element that can be included in a prostatic stent 10 is a removal segment 24. The removal segment 24 is a long thin member such as a suture that extends from the bulbar segment 12 and terminates outside of the patient's body when the prostatic stent 10 is placed within the urinary system of the patient. The removal segment 24 has a first end and a second end. The first end of the removal segment 24 is embedded or secured to the prostatic stent 10 in such a way as to form a connection without hanging ends, rough discontinuities, or other jagged surfaces that would collect blood clots and/or other bodily material. Both FIGS. 1K and L show the connection between the removal segment 24 and the bulbar segment 12. FIG. 1K is an enlarged perspective view of the removal segment 24 embedded within the wall of the bulbar segment 12. The first end of the removal segment 24 lies within the wall of the bulbar segment 12, and no portion of the removal segment 24 is attached or located on the exterior wall of the bulbar segment 12. The first end of the removal segment 24 may be tied into a knot or folded over into a hook prior to being embedded within the prostatic segment 14. The knot or hook at the first end of the removal segment 24 increases the tensile strength of the removal segment 24 by creating a greater amount of surface area contact between the removal segment 24 and the bulbar segment 12. FIG. 1L shows a cross-sectional view taken along line FF in FIG. 1A of the removal and bulbar segments 24, 12. The second end of the removal segment 24 remains outside of the patient's body and is useful to a medical professional during the placement and removal of the prostatic stent 10 within the patient's body. When inserting the prostatic stent 10, the medical professional restrains the second end of the removal segment 24 keeping it taut so that the connecting segment 20 does not buckle. By restraining the second end of the removal segment 24, the medical professional ensures that the prostatic and bulbar segments 12, 14 are properly separated such that when the prostatic stent 10 is positioned within the patient's body the prostatic segment 14 will be located on the proximal side of the patient's external sphincter and the bulbar segment 12 will be located on the distal side of the external sphincter. To remove the prostatic stent 10, the medical professional simply pulls on the second end of the removal segment 24 to dislodge the prostatic stent 10 from its placement within the patient's body.

Figure 2:
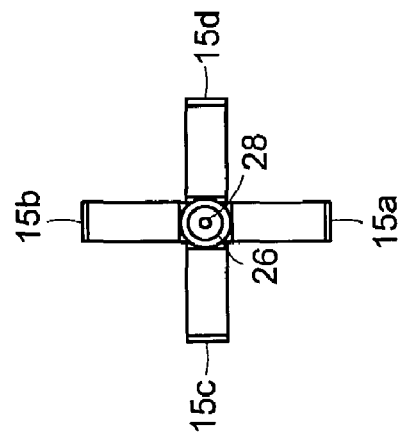
FIG. 2 is a top view of a prostatic stent including a proximal tip that is straight.
Figure 3:
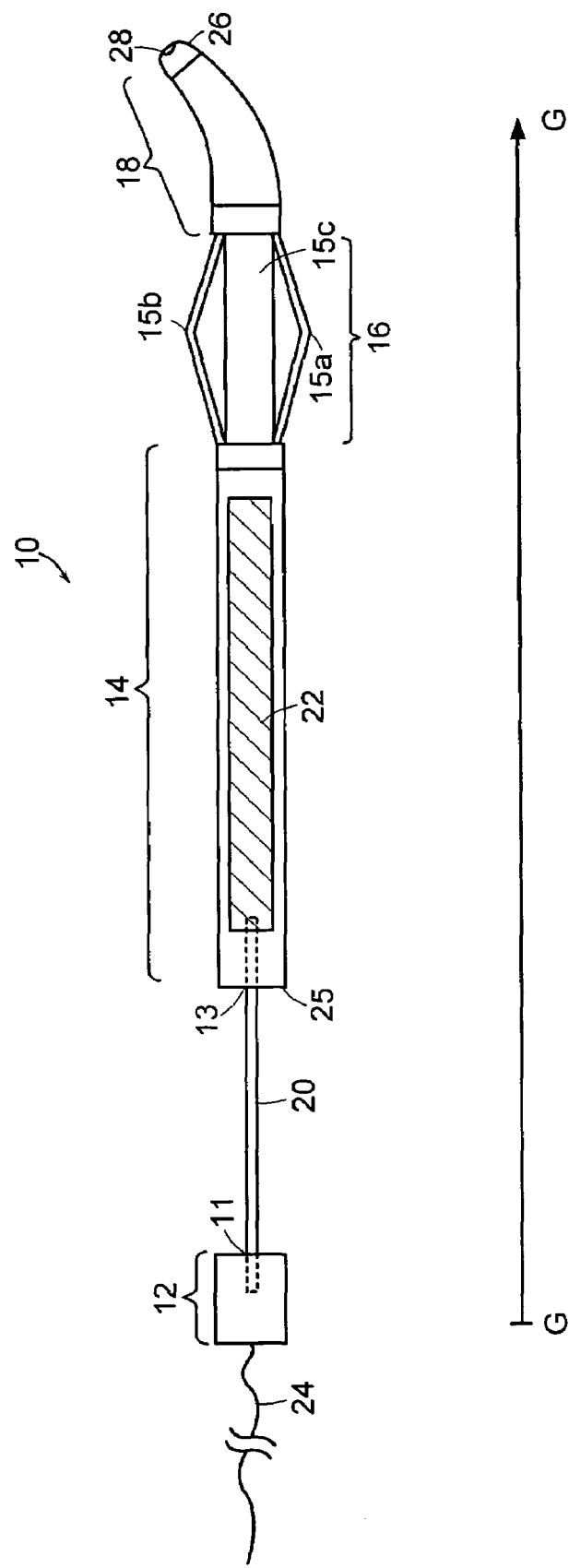
FIG. 3 is a side view of a prostatic stent with a multi-winged malecot in a collapsed configuration.

Prostatic stents according to the invention include at least one anchor to prevent the migration of the prostatic stent 10 after it has been properly positioned within the body. In the disclosed embodiment, there are two anchors. The multi-winged malecot 16 prevents the distal migration of the prostatic stent 10 (down out of the bladder and out of the patient's urinary system), while the bulbar segment 12 prevents the proximal migration (up into the bladder). The arrangement of the malecot wings 15a-d is shown in FIG. 2. FIG. 2 shows a top view of the prostatic stent 10 of FIG. 1A, but with a modification. The proximal tip 18 in FIG. 1A is curved, but in FIG. 2 the proximal tip 18 is straight. In the disclosed embodiment, the multi-winged malecot 16 has four wings 15a-d, in other embodiments the multi-winged malecot 16 could have two or more wings to prevent the distal migration of the prostatic stent 10. The multi-winged malecot 16 has at least two distinct configurations, an expanded configuration and a collapsed configuration. In FIGS. 1A and 2, the multi-winged malecot 16 is in the expanded configuration. The multi-winged malecot 16 is biased in the expanded configuration and therefore will return to this configuration in the absence of external compressive forces acting upon it. FIG. 3 shows a prostatic stent 10 with its multi-winged malecot 16 in the collapsed configuration. To achieve the collapsed configuration, the medical professional extends the proximal tip 18 of the prostatic segment 14 along a directional line labeled GG in FIG. 3. Generally, the multi-winged malecot 16 on the prostatic stent 10 is in the collapsed configuration during insertion so as not to injure the patient's urethra.

Figure 4:
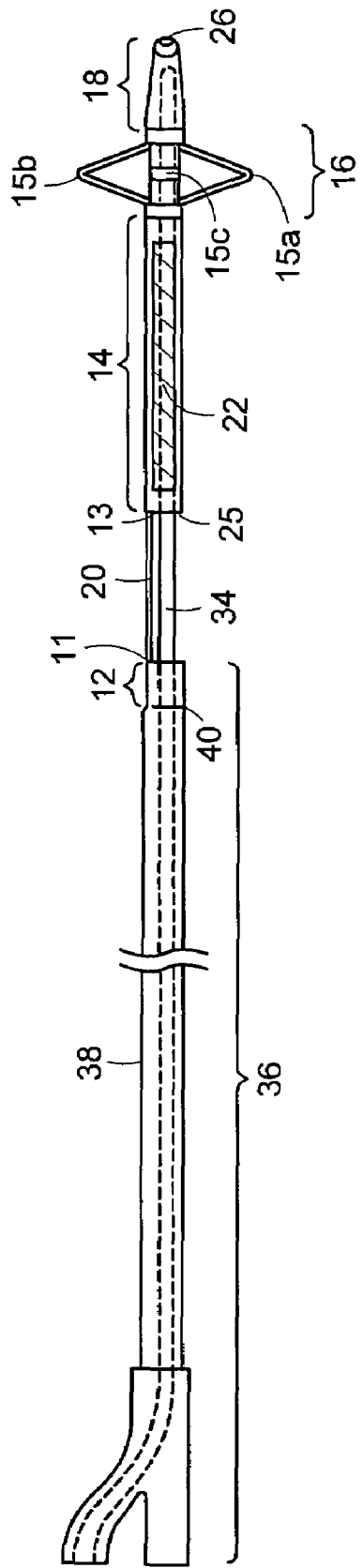
FIG. 4 is a side view of a prostatic stent connected to a delivery system.

To place the prostatic stent 10 in the proper position within the patient's body, the medical professional can use a delivery system 36. A schematic of one embodiment of a delivery system 36 connected to the prostatic stent 10 is shown in FIG. 4. The delivery system 36 includes a stylet 34, which is a long tubular member with two ends for advancing the prostatic stent 10 through the patient's urethra and a delivery tube 38 partially surrounding the stylet 34. The stylet can be made from a biocompatible material that is flexible enough to conform to the patient's body, but also rigid enough to push the prostatic stent 10 through the patient's urinary system. The width of the stylet 34 is sized to fit within the lumens of both the bulbar segment 12 and the prostatic segment 14. The length of the stylet 34 is sized so that one end of the stylet 34 can contact the proximal tip 18 of a prostatic stent 10 that is properly positioned within the body of the patient, while the other end remains external to the patient's body. Within the stylet 34 there is a lumen extending along the longitudinal axis of the stylet 34. This lumen is sized to receive a guide wire to aid in the insertion processes as well as to convey a fluid such as urine from the patient's bladder. The delivery tube 38 is made from a biocompatible material and provides rigidity to the delivery system 36. The medical professional inserting the prostatic stent 10 and the delivery system 36 can use the delivery tube 38 as a handle to the connected delivery system 36 and prostatic stent 10 during placement of the prostatic stent 10. The delivery tube 38 is not as long as the stylet 34. The length of the delivery tube is sized so that a proximal terminating end 40 does not extend past the bulbar segment 12 of the prostatic stent 10. The outer diameter of the delivery tube 38 is substantially the same size as the outer diameter of the bulbar segment 12 of the prostatic stent 10. In the disclosed embodiment, the proximal terminating end 40 terminates just prior to a distal end of the bulbar segment 12 when the prostatic stent 10 and delivery system 36 are connected. In other embodiments, the proximal terminating end 40 can be tapered to dovetail with the bulbar segment 12 so that during insertion the proximal terminating end 40 of the delivery tube 38 is located within the lumen of the bulbar segment 12.

Figure 5:
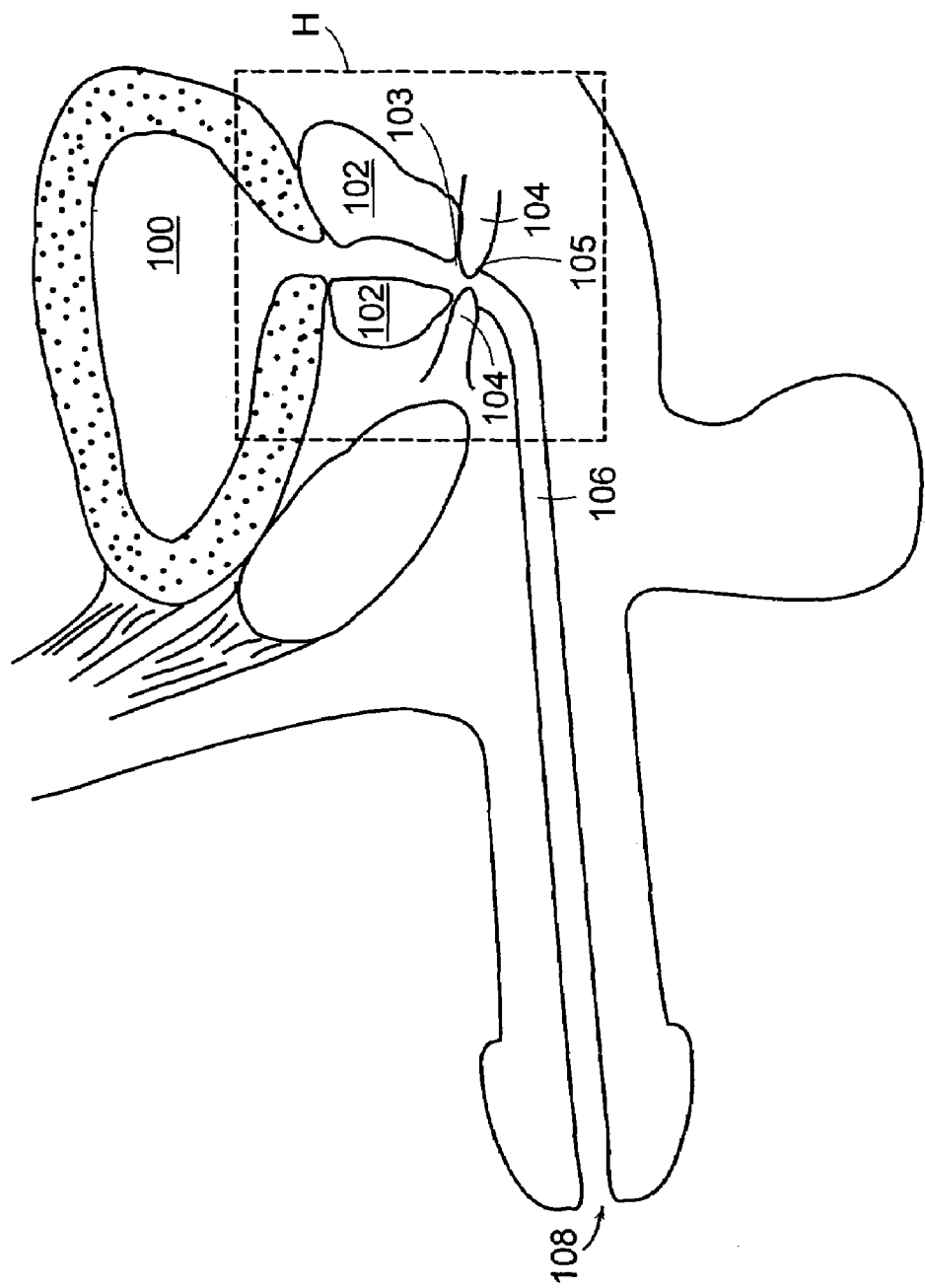
FIG. 5 is a schematic view of a male patient's urinary system.

The medical professional tending to the patient suffering from bladder outlet obstruction inserts the prostatic stent 10 and delivery system 36 into the patient's urethra 106 at the meatus 108. (Refer to, FIG. 5 for a schematic representation of the male urinary system.) The medical professional uses the stylet 34 to advance the proximal tip 18 of the prostatic stent 10 along the urethra 106 past the external sphincter 104 and into the bladder 100. The medical professional then further advances the prostatic stent 10 such that the multi-winged malecot 16 is located in the bladder 100, the prostatic segment 14 is in the section of the urethra 106 surrounded by the prostate 102 with its distal end 25 located just prior to the proximal side of the patient's external sphincter 103, and the bulbar segment 12 is located on the distal side of the patient's external sphincter 105. At this point, the stylet 34 extends from the bladder through the urethra and terminates at a location external to the patient's body. To confirm correct placement of the prostatic stent 10, the medical professional looks for urine flowing from an end of the stylet 34 located external to the patient's body.

Figure 6:
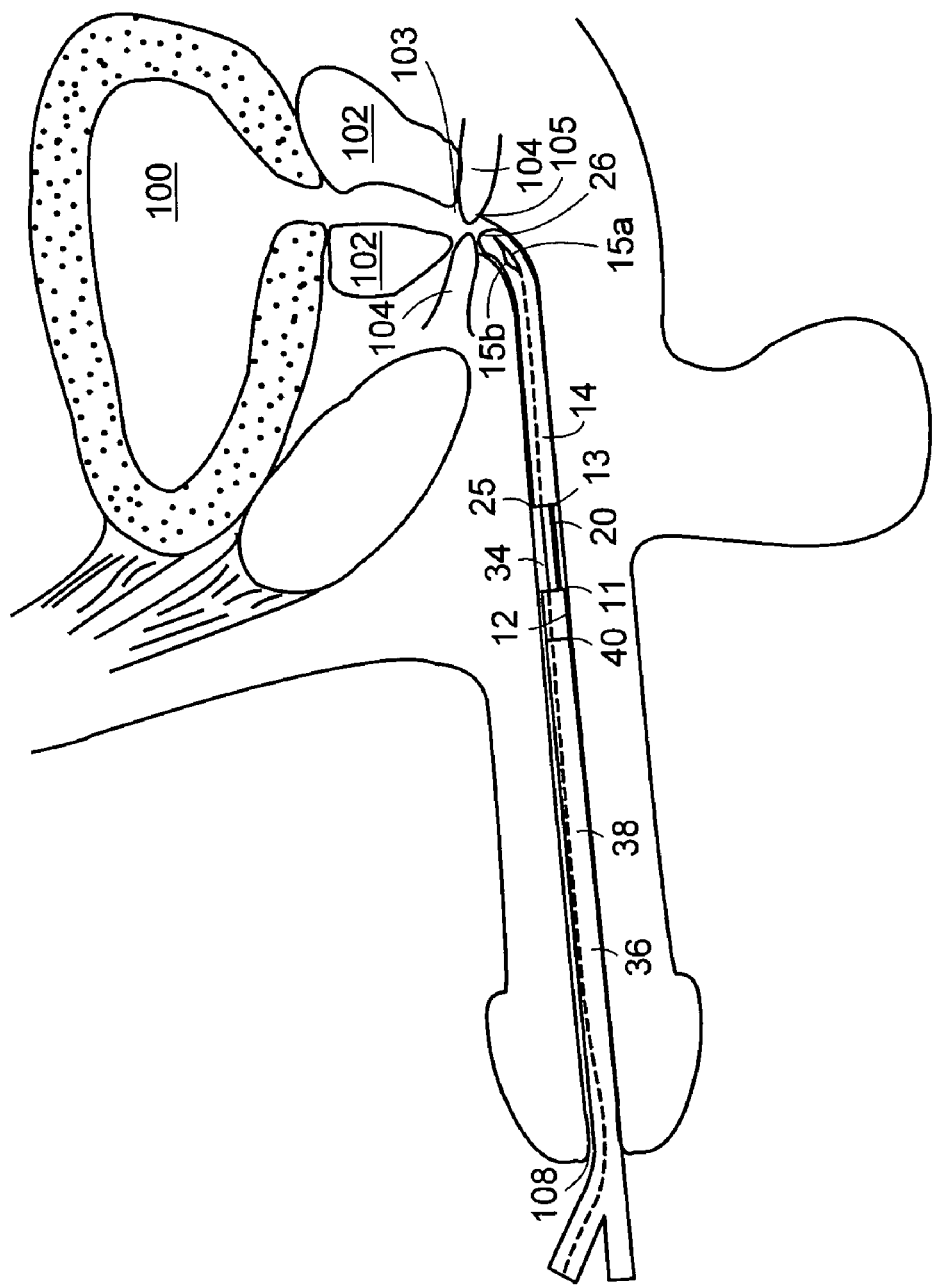
FIG. 6 is a schematic view of a prostatic stent connected to a delivery system being inserted into the male patient's urinary system.
Figure 7:
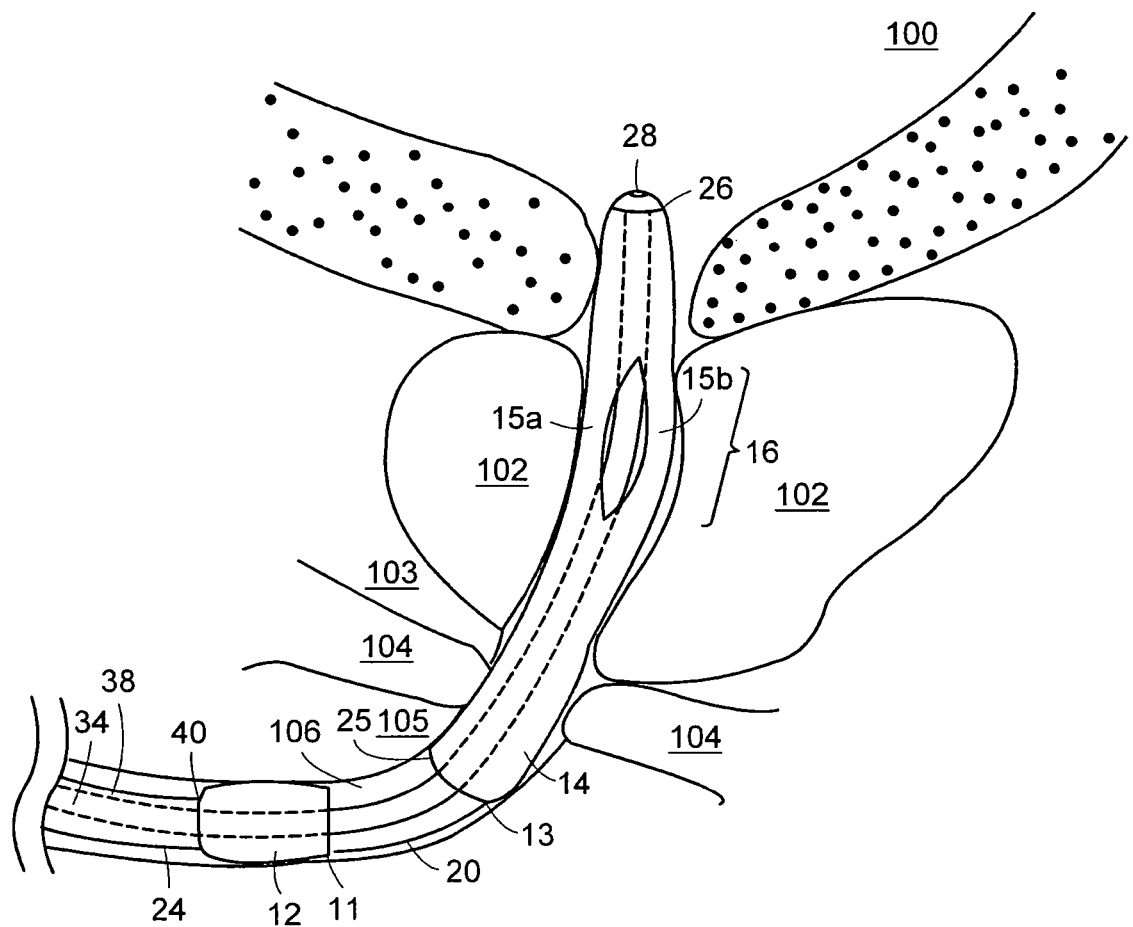
FIG. 7 is an expanded view of a prostatic stent within the male patient's urinary system.
Figure 8:
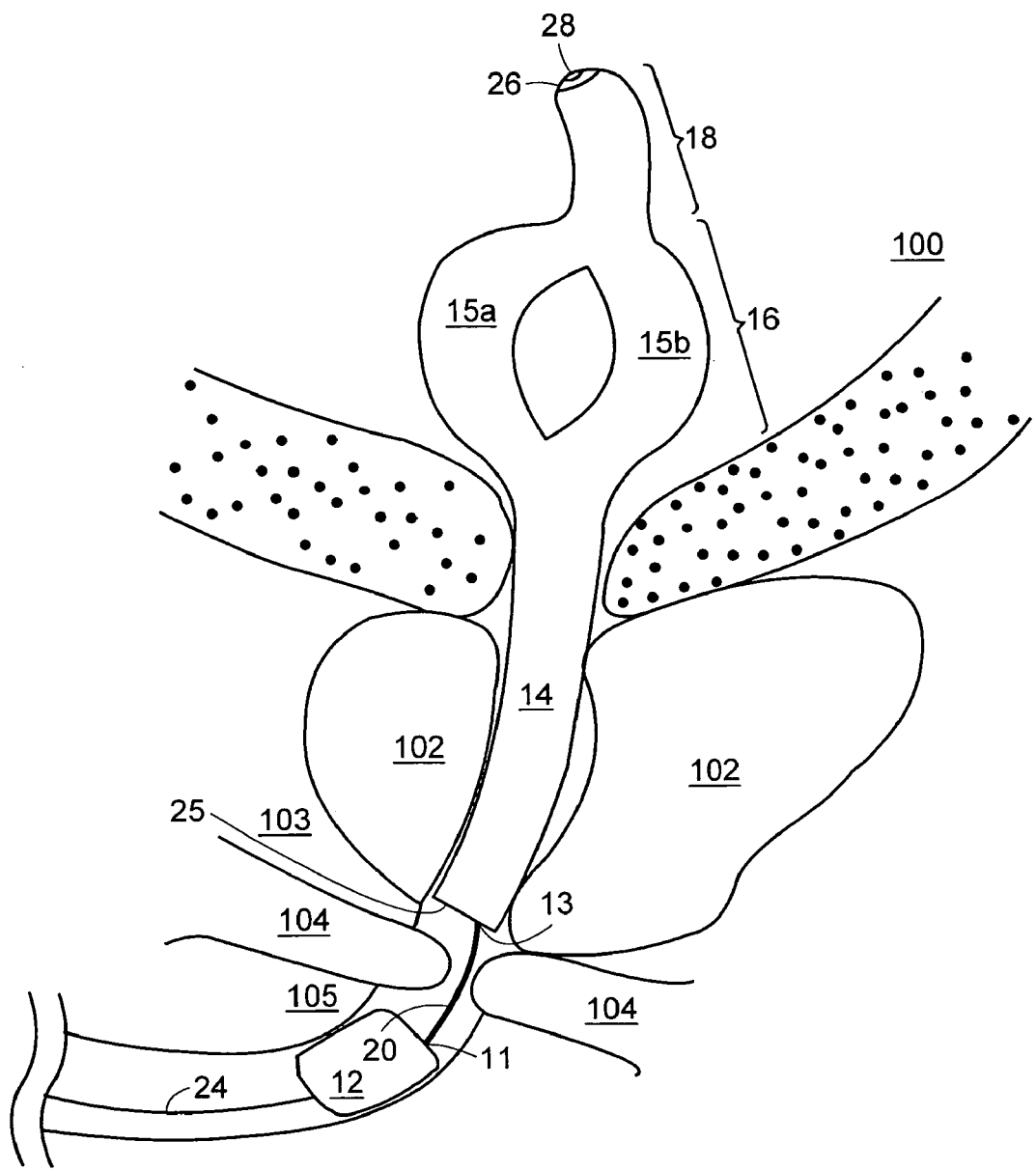
FIG. 8 is another expanded view of a prostatic stent with a multi-winged malecot in an expanded configuration and located within the bladder.

Prior to insertion of the prostatic stent 10, the medical professional places the multi-winged malecot 16 into the collapsed configuration to allow for the passage of the prostatic stent 10 through the urethra 106. FIG. 6 shows the prostatic stent 10 and the delivery system 36 being inserted into the urethra 106 with the multi-winged malecot 16 in the collapsed configuration. The multi-winged malecot 16, remains in the collapsed position as long as there is an external force acting to collapse the wings of the malecot 15a-d. FIG. 7 is an expanded view of the prostatic stent 10 within an area marked H on FIG. 5. It should be noted that the wings of the malecot 15a-b (15c-d are not visible in this view) are collapsed due to the proximal extension of the proximal tip 18 of the prostatic stent 10 by the stylet 34 and to the compressive force on the malecot wings 15a-b created by the urethra 106. The prostatic stent 10 is further advanced by the stylet 34 of the delivery system 36 until the prostatic stent 10 is located in the proper position. After the medical professional confirms proper positioning, he or she retracts the stylet 34. FIG. 8 shows the prostatic stent 10 properly positioned within the urinary system of the patient. It is important to note that the stylet 34 is no longer contacting or extending the proximal tip 18 and that the wings 15a-b are no longer compressed by the urethra 106 or any other body part. Therefore, the wings 15a-b naturally expand thereby anchoring the prostatic stent 10 in the bladder 100 and preventing the distal migration of the prostatic stent 10. Once the prostatic stent 10 is properly positioned, the delivery system 36 is completely removed from the patient's urethra 106.

Figure 9A:
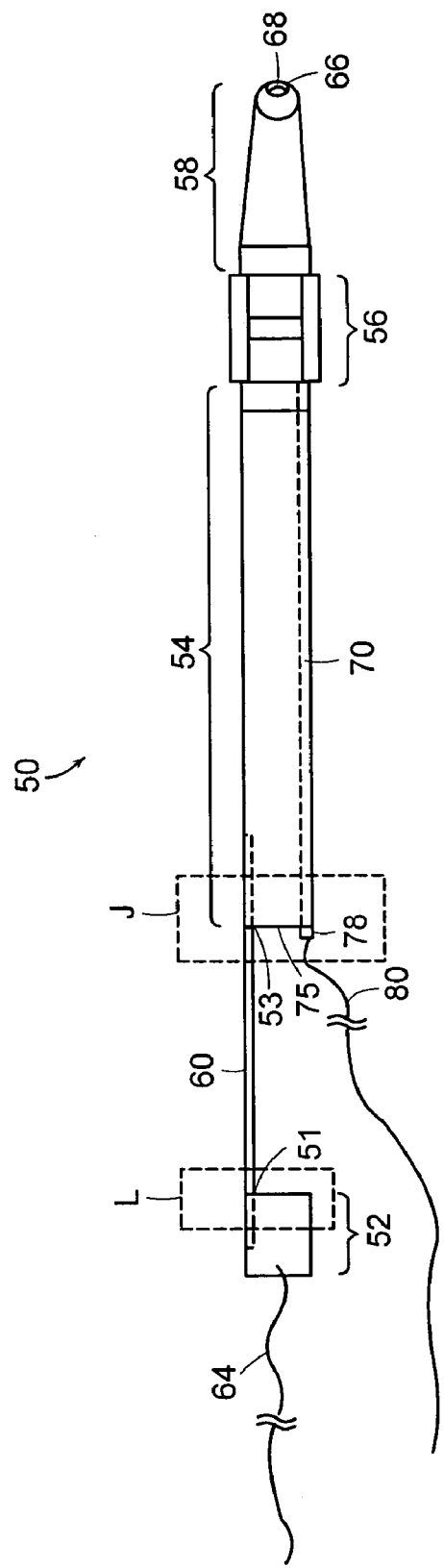
FIG. 9A is a side view of one embodiment of a prostatic stent with an inflatable balloon shown in an insertion configuration.
Figure 10:
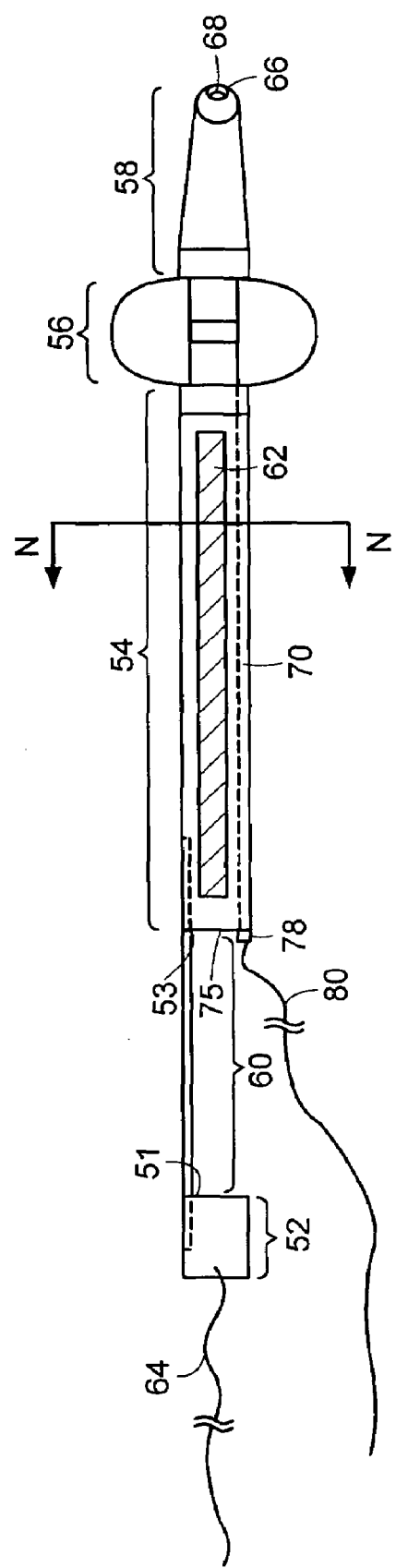
FIG. 10 is a side view of the prostatic stent of FIG. 9A with the inflatable balloon shown in an expanded configuration.

Another embodiment of a prostatic stent 50 is shown in FIGS. 9A and 10. In this embodiment, the prostatic stent 50 includes a bulbar segment 52, a prostatic segment 54, an inflatable balloon 56, and a connecting segment 60. The bulbar and prostatic segments 52, 54 are tubular elements, each having a lumen sized for conveying fluids. The bulbar and prostatic segments 52, 54 are both made from biocompatible materials, such as silicone, which are sufficiently flexible to conform to the shape of the urethra 106 for insertion ease while simultaneously are also sufficiently rigid to maintain an open passageway through the urethra 106. In the disclosed embodiment, the cross-sectional shape of the bulbar and prostatic segments 52, 54 is circular, however in other embodiments the cross-sectional shape could be elliptical, rectangular, triangular or square. FIG. 9A shows the prostatic stent 50 in an insertion configuration (with an unfilled inflatable balloon). FIG. 10 shows the prostatic stent 50 in an expanded configuration with a filled inflatable balloon. To fill the inflatable balloon with a fluid, the prostatic stent 50 also includes an inflation channel 70 that extends from a one-way valve 78 located at the distal end 75 of the prostatic segment 54 through the wall of the prostatic segment 54 and terminates within the inflatable balloon 56. The one way valve 78 allows fluids such as air or saline to only pass into the inflatable balloon. To deflate the balloon after it has been filled, the one way valve 78 can be removed, thereby allowing the fluid to escape from the inflation channel 70 and the inflatable balloon 56. Attached to the one way valve 78 is a removal suture 80 used for disconnecting the one way valve 78 from the inflation channel 70. To remove the one way valve 78 from the inflation channel 70 the medical professional simply pulls on the removal suture 80.

Figure 9B:
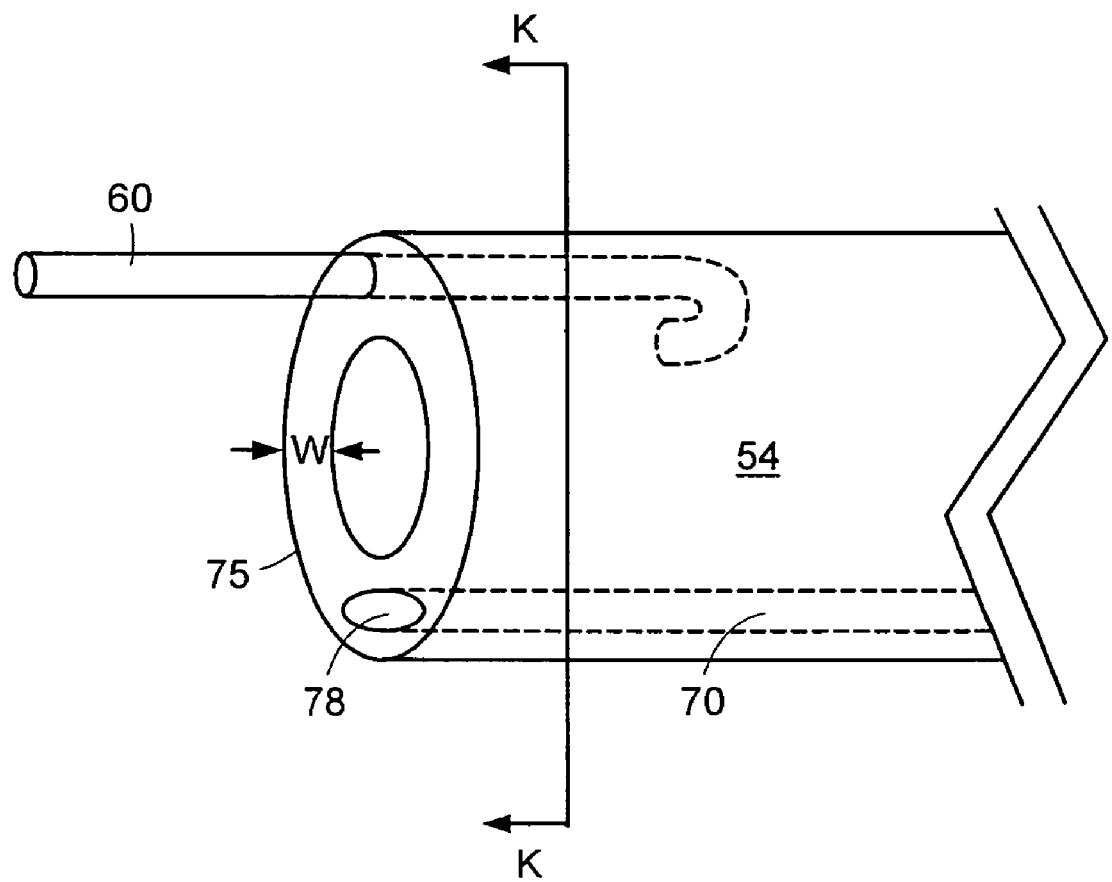
FIG. 9B is an enlarged side view of a section of the prostatic stent shown in FIG. 9A.
Figure 9C:
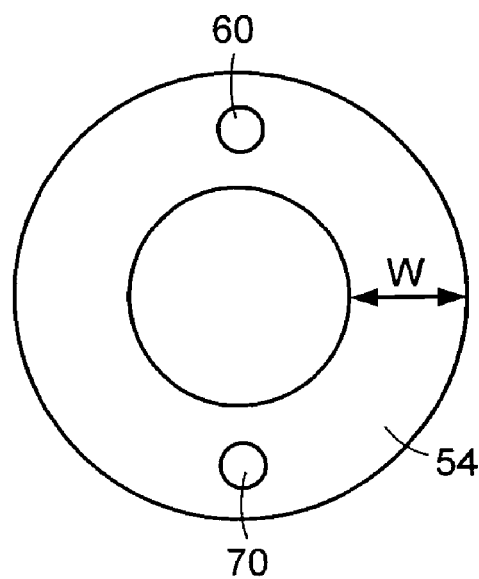
FIG. 9C is an enlarged cross-sectional view of the prostatic stent taken along line KK in FIG. 9B.

When the prostatic stent 50 is properly positioned within the male patient's urinary system, the inflatable balloon 56 is located within the bladder 100 near the bladder opening, the prostatic segment 54 is located substantially within the prostatic urethra with the distal end 75 of the prostatic segment 54 terminating just prior to the proximal side of the patient's external sphincter 103, and the bulbar segment 53 is located on the distal side of the external sphincter 105. The connecting segment 60 couples the prostatic segment 54 to the bulbar segment 52 and is sized to extend through the external sphincter 104 without interfering with the normal operation of the external sphincter such that the patient has control over bladder voiding and retention. The connecting segment 60 in the embodiment shown in FIG. 9A is a stainless steel wire coated in silicone. One end of the wire is embedded in the bulbar segment 54 while the other end is embedded within the prostatic segment 54. To increase the tensile strength of the connecting segment 60, the ends of the wire may be bent or folded into the shape of a hook, a "L", or any other shape that provides a greater amount of contact surface area between the connecting segment 60 and the bulbar and prostatic segments 52, 54. The connecting segment 60 can also be made from other biocompatible materials such as titanium, a suture, or a strip of a biocompatible polymer or other material that is thin enough to extend through the external sphincter without negatively affecting its normal operation and that is strong enough to couple together the prostatic and bulbar segments 52, 54. Transitions 51, 53 between the bulbar, connecting, and prostatic segments 52, 60, 54 should be smooth and free from jagged surfaces and hanging ends on the exterior surfaces of the segments 52, 60, 54 that would collect blood clots and other debris. FIG. 9B shows an enlarged side view of a section of the prostatic stent 50 labeled J. In this view, the transition 53 between the connecting and prostatic segments 60, 54 is visible. One of the ends of the connecting segment 60 is embedded within the wall of the prostatic segment 54, and is secured within the prostatic segment 54 by, for example, use of an adhesive or heat bonding the connecting segment 60 to the prostatic segment 54. The transition 53 is smooth and free of discontinuities or edges that would collect blood clots or other bodily materials. FIG. 9C, which is a cross-sectional view taken along line KK in FIG. 9B, shows the location of both the connecting segment 60 and the inflation channel 70 within the prostatic segment 54.

Figure 9E:
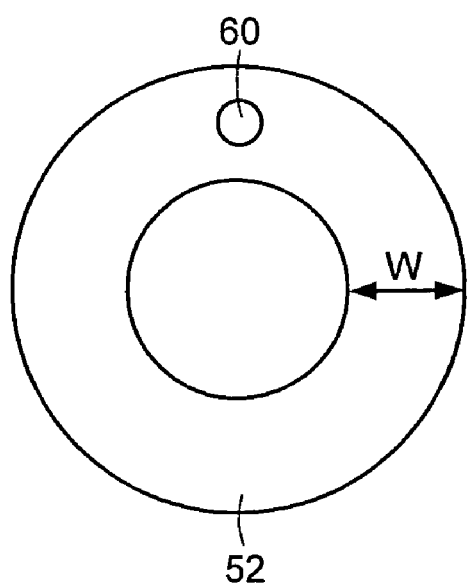
FIG. 9E is an enlarged cross-sectional view of the prostatic stent taken along line MM in FIG. 9D.
Figure 9D:
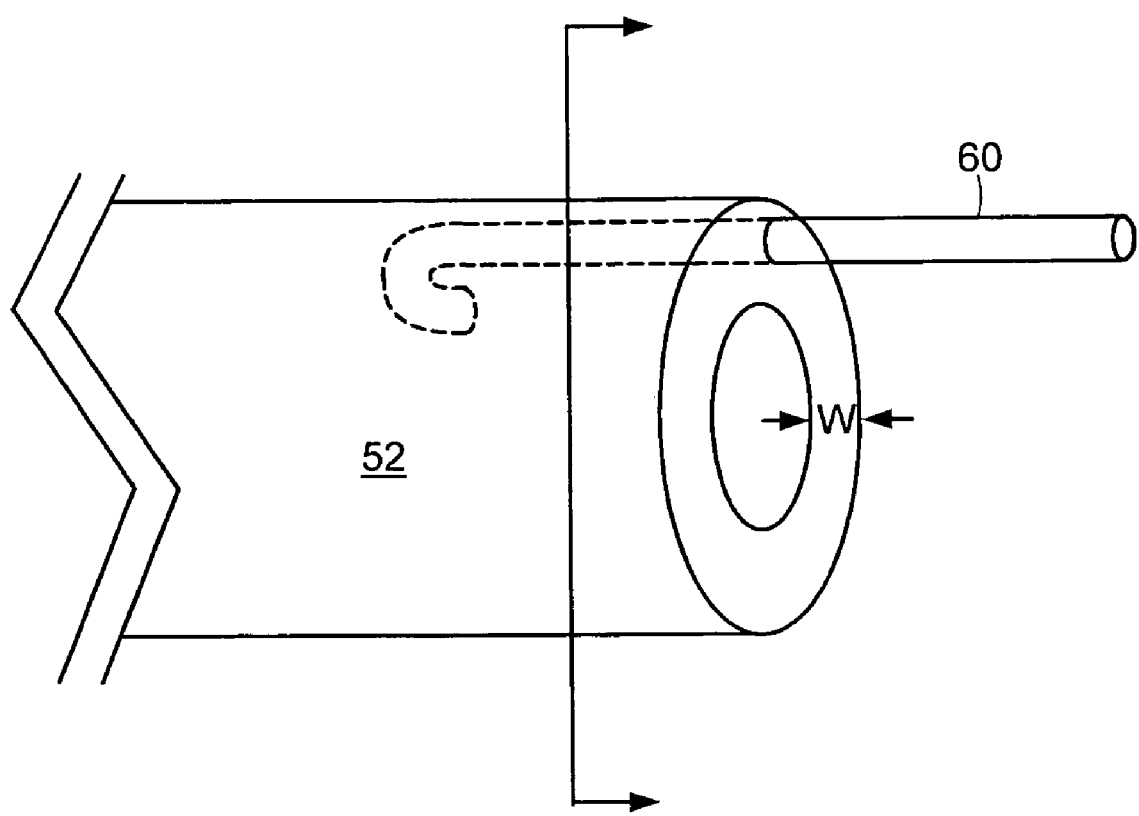
FIG. 9D is another enlarged side view of a section of the prostatic stent shown in FIG. 9A.

The transition 51 between the bulbar and connecting segments 52, 60 is also smooth. The other end of the connecting segment 60 is attached to the bulbar segment 52 in such a way as to not pierce or puncture through the exterior wall of the bulbar segment 52. FIGS. 9D and 9E show enlarged perspective and cross-sectional views of the transition 53. FIG. 9D shows an enlarged view of a section of the prostatic stent 50 which is labeled L in FIG. 9A. FIG. 9E shows a cross-sectional view taken along line MM in FIG. 9D. As shown in FIGS. 9D and 9E, the transition 51 is smooth and free of jagged surfaces and/or hanging ends that would attract blood clots or other debris.

Referring to FIG. 9A, the prostatic stent 50 further includes a proximal tip 58. The proximal tip 58 has a proximal end 66 and can be either straight as shown in FIGS. 9A and 10, or curved. Extending within the proximal tip 58 and the inflatable balloon 56 is a lumen that is in communication with the lumen of the prostatic segment 54. The proximal tip 58 further includes an opening 68 in communication with the lumen extending within the proximal tip 58. The opening 68 is sized to accept fluid from the bladder 100 of the patient, as well as to accept a guide wire. In other embodiments, the proximal tip 58 may include more than one opening 68 in communication with the lumen within the proximal tip 58 to drain fluids such as urine and/or blood from the patient's bladder 100.

Figure 11A:
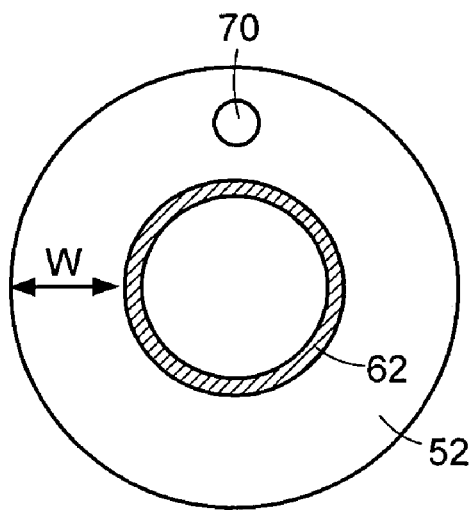
FIG. 11A is an enlarged cross-sectional view of the prostatic stent taken along line NN in FIG. 10 showing a reinforcing element lying against an interior wall of a prostatic segment.
Figure 11B:
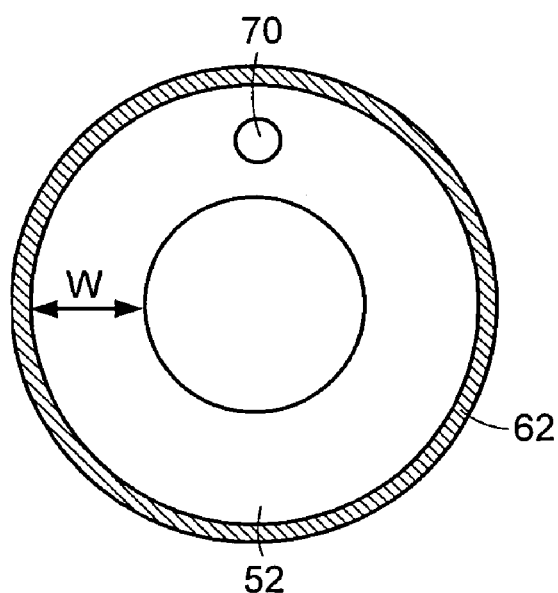
FIG. 11B is another enlarged cross-sectional view taken along line NN in FIG. 10 showing a reinforcing element lying against an exterior wall of the prostatic segment.
Figure 12:
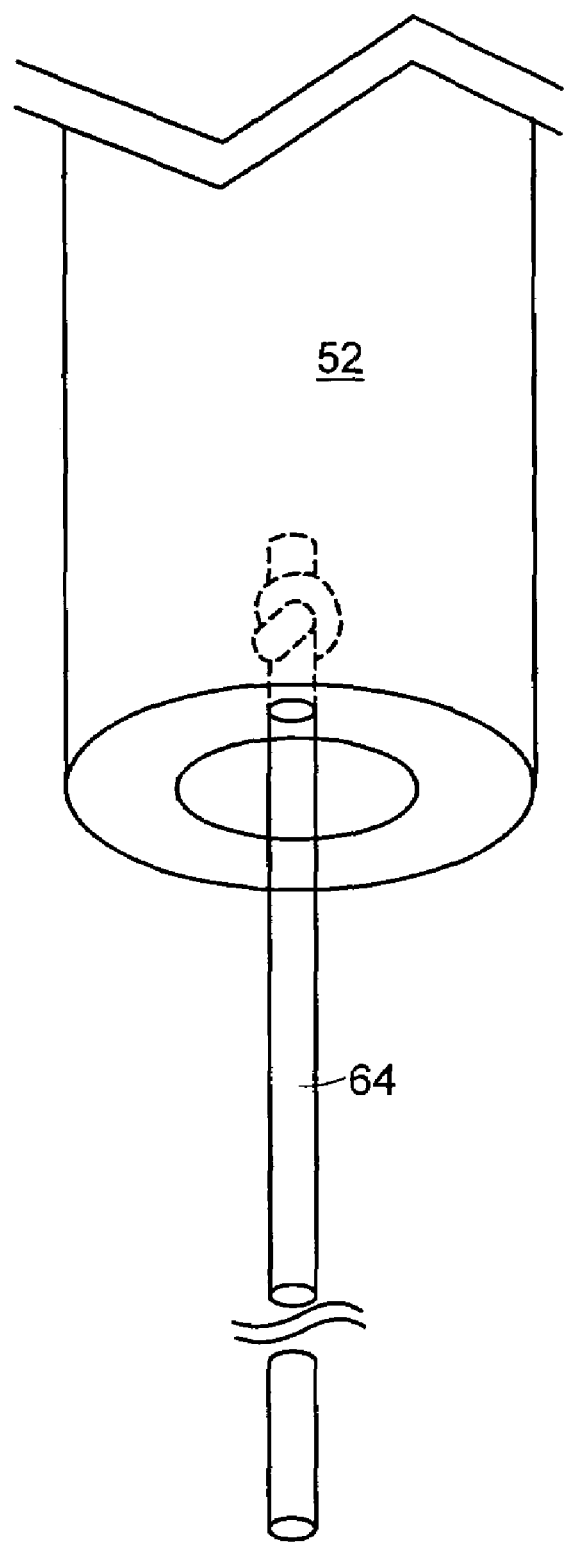
FIG. 12 is an enlarged view of a removal segment embedded within a bulbar segment.

In another embodiment, the prostatic stent 50 can include a reinforcing element 62 as shown in FIG. 10. Embodiments of reinforcing elements 62 can include a metallic coil or wire mesh tube or other strength-adding member(s) such as, for example, multiple spaced bands of metal to increase the tensile strength of the prostatic segment 54. Generally, the reinforcing element 62 lies against either the interior wall that defines the lumen of the prostatic segment 54 or the exterior wall that defines the outer diameter of the prostatic segment 54 so as not to interfere with the inflation channel 70. FIGS. 11A and B are a cross-sectional views of the prostatic stent 50 taken along line NN in FIG. 10 showing two different possible placements of the reinforcing element 62. FIG. 11A shows the reinforcing element 62 positioned against the interior wall of the prostatic segment 54, whereas FIG. 11B shows the reinforcing element 62 positioned against the exterior wall of the prostatic segment 54. The reinforcing element 62 may be coated with silicone or any other biocompatible polymer to prevent the collection of bodily materials on the reinforcing element 62. Another element than can be included in the prostatic stent 50 is a removal segment 64, which is a useful tool to a medical professional during placement (i.e., keeping the prostatic and bulbar segments 54, 52 properly separated) and removal of the prostatic stent 50 within the body of the patient. In the preferred embodiment, the removal segment 64 would be embedded or secured to the prostatic stent 50 in such a way as to not produce hanging ends or other edges on the exterior surface of the bulbar segment 52 that would collect blood clots or other debris as shown in FIG. 12.

Figure 13:
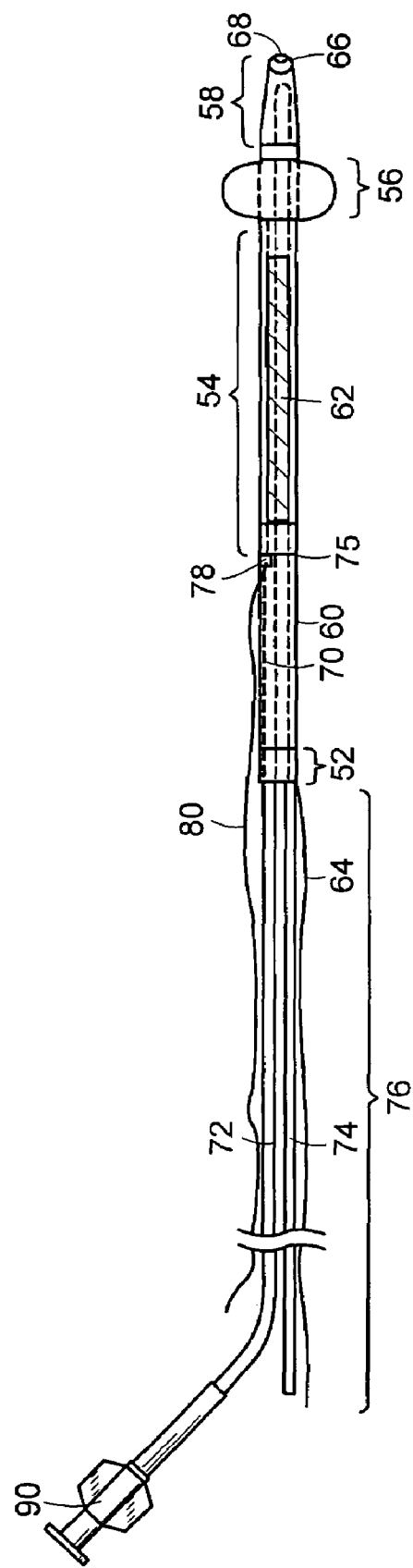
FIG. 13 is a side view of a prostatic stent connected to a delivery system.
Figure 14:
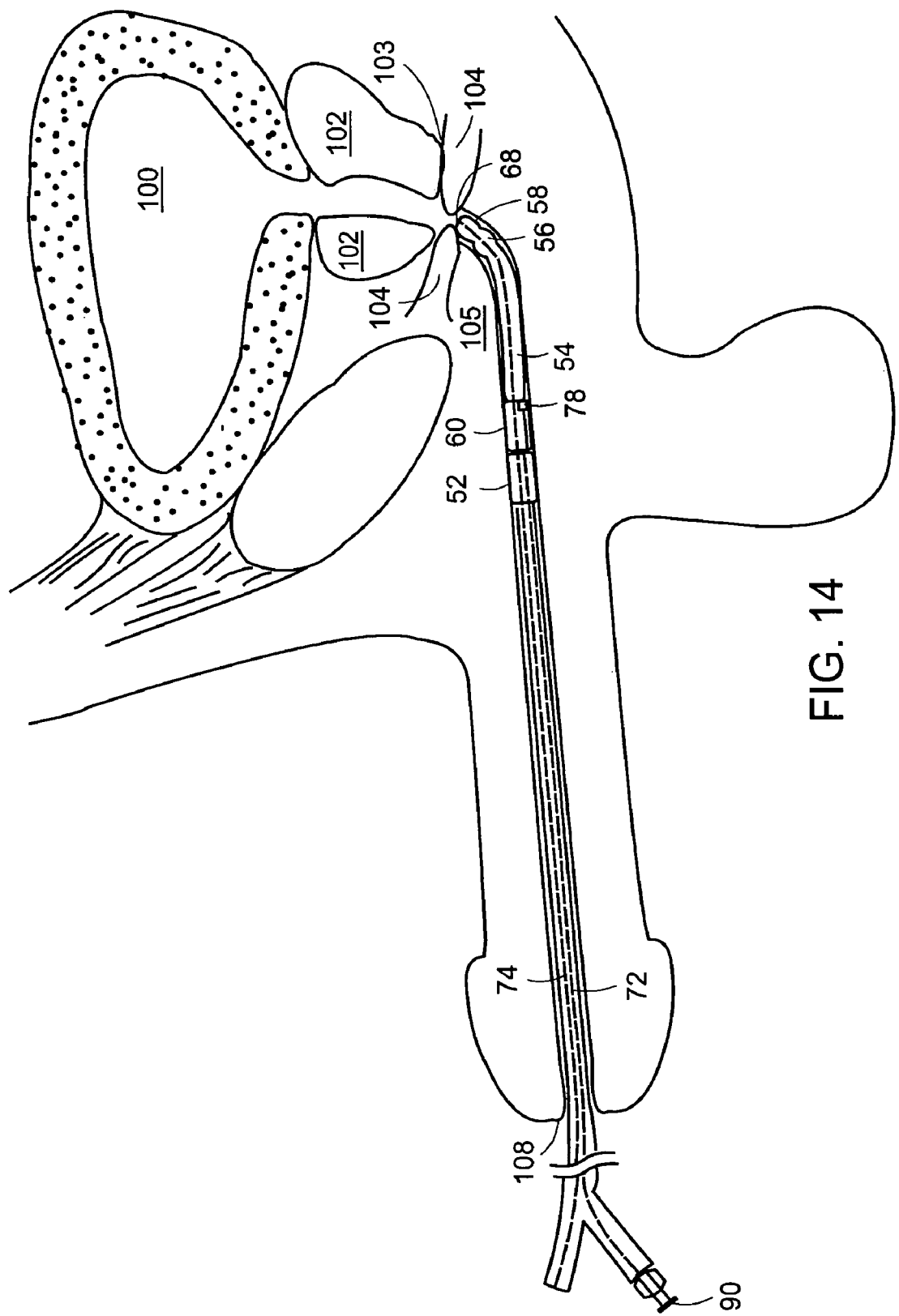
FIG. 14 is a schematic view of a prostatic stent connected to a delivery system being inserted into the male patient's urinary system.
Figure 15:
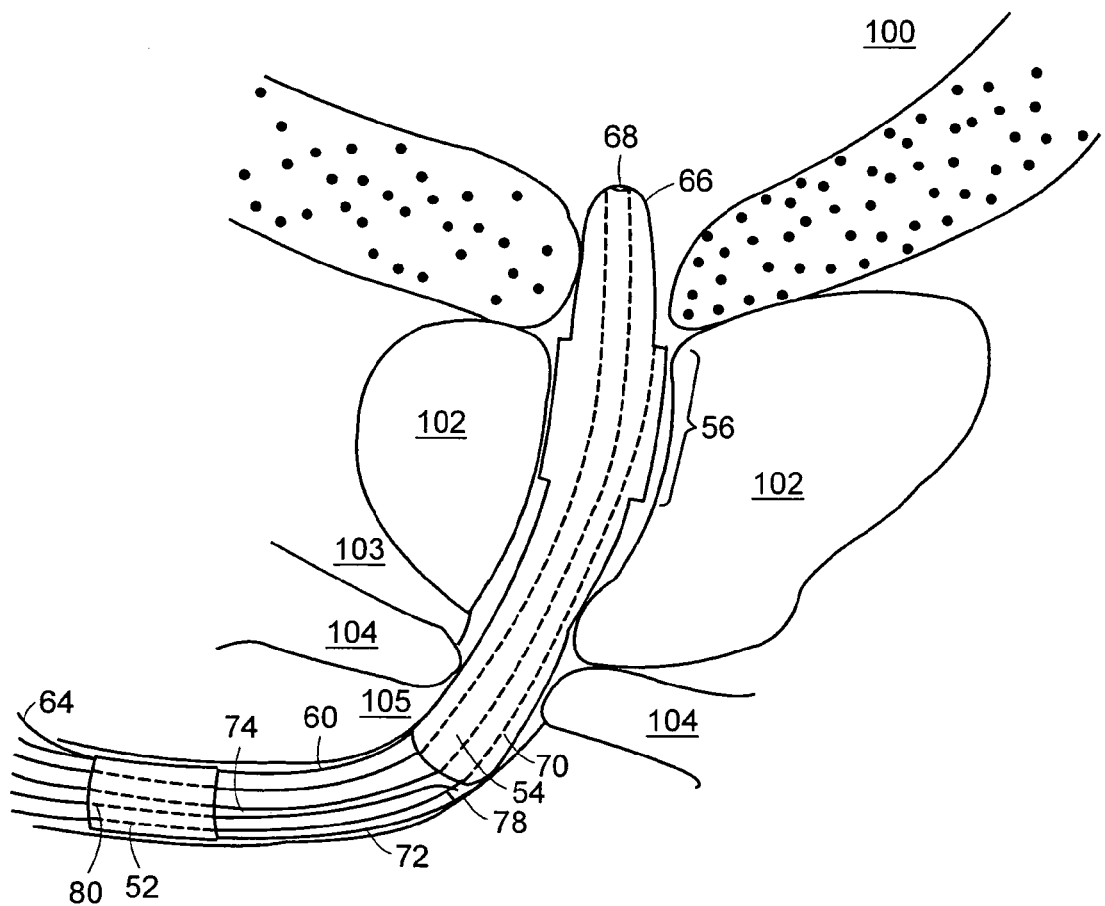
FIG. 15 is an expanded view of a prostatic stent within the male patient's urinary system.
Figure 16:
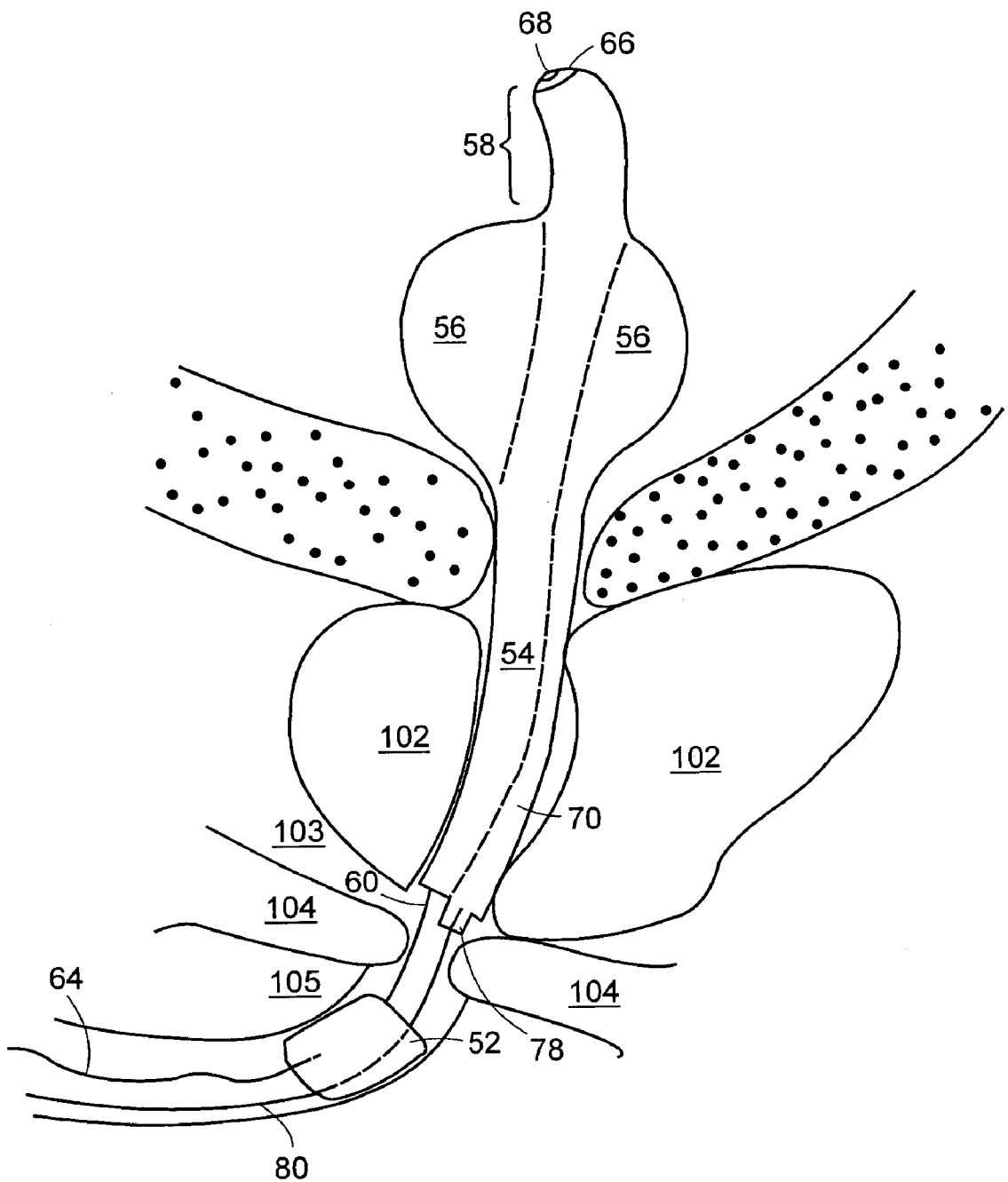
FIG. 16 is another expanded view of a prostatic stent with a inflatable balloon in an expanded configuration and located within the bladder.

In the disclosed embodiment, a delivery system 76 including a stylet 74 and an inflation line 72 connected to a syringe 90 is used by a physician or other medical professional to properly position the prostatic stent 50 within the urinary system of the patient. In another embodiment, the delivery system 76 could further include a delivery tube similar to the delivery tube 38 shown in FIG. 4. Likewise, the delivery tube would be made from a biocompatible material and would provide rigidity to the delivery system 76. A schematic of the disclosed embodiment of the delivery system 76 used with prostatic stent 50 is shown in FIG. 13. The stylet 74, a long thin member sized to fit within the lumens of the bulbar segment 52 and the prostatic segment 54, is used for advancing the prostatic stent 50 through the patient's urinary system until the inflatable balloon 56 is located within the bladder 100. The inflation line 72 is a tube for conveying fluid from the syringe 90 to the inflation channel 70. Prior to inserting the prostatic stent 50 and the delivery system 76 into the patient's urinary system, the inflation line 72 is connected to the one way valve 78 and the stylet 74 is passed through the lumens of the bulbar and prostatic segments 52, 54 to connect the delivery system 76 to the prostatic stent 50. After the prostatic stent 50 and the delivery system 76 are connected, the medical professional inserts the proximal tip 58 of the prostatic stent 50 into the urethra 106 of the patient at the meatus 108. FIG. 14 shows the prostatic stent 50 in the insertion configuration (unfilled inflatable balloon) and the delivery system 76 inserted within the urethra 106. FIG. 15 is an expanded view of the prostatic stent 50 within the area marked H in FIG. 5. It should be noted that the prostatic stent 50 is in the insertion configuration while in this location. The prostatic stent 50 is further advanced through the patient's urethra 106 until the inflatable balloon 56 is within the bladder 100. FIG. 15 shows an expanded view of the prostatic stent 50 within the bladder 100. To confirm placement within the bladder 100, the medical professional looks for urine flowing from an external end of the delivery system 76. Once the inflatable balloon 56 is within the bladder 100, the medical professional uses the syringe 90 to insert a fluid such as saline or air into the inflation line 72. The fluid flows through the inflation line 72, through the one way valve 78 and inflation channel 70, and into the inflatable balloon. After the inflatable balloon 56 is filled, the inflation line 72 and stylet 74 are removed from the patient's urethra 106. FIG. 16 shows an expanded view of the prostatic stent 50 within the bladder 100 after the balloon has been filled (the expanded configuration) and the inflation line 72 and stylet 74 have been removed. The balloon in the expanded configuration anchors and prevents the distal migration of the prostatic stent 50.

The prostatic stent 50 can be removed from the patient's separately at some later time, by first deflating the inflatable balloon 56, and then removing the prostatic stent 50. To deflate the inflatable balloon 56, the one way valve 78 is disconnected from the prostatic stent 50 by pulling on the removal suture 80. After the one way valve 78 is removed the fluid within the inflatable balloon 56 will be able to exit the prostatic stent 50 through the inflation channel 70. With the inflatable balloon 56 deflated, it no longer serves as an anchor to inhibit removal of the prostatic stent 50, and thus the prostatic stent 50 can be removed by either pulling on the removal segment 64 or through endoscopic means.

Figure 17A:
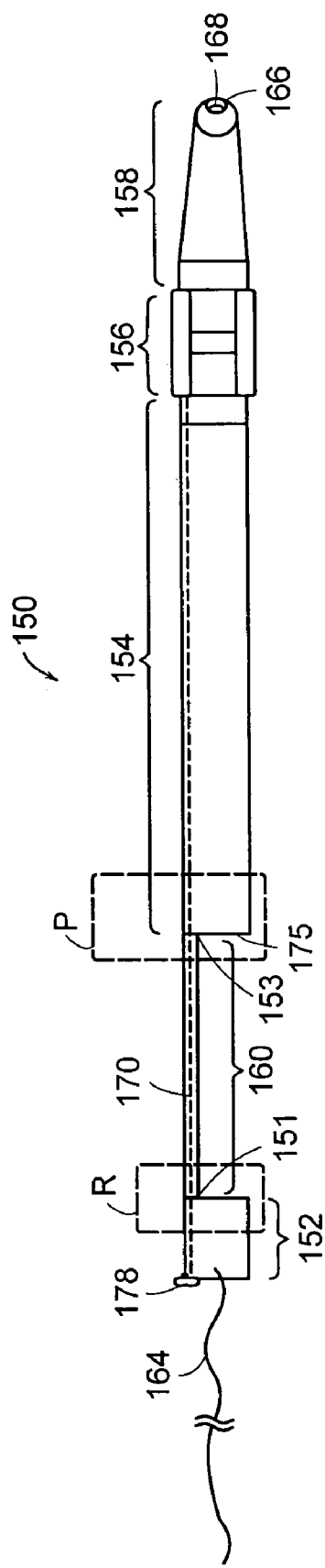
FIG. 17A is a side view of another embodiment of a prostatic stent with an inflatable balloon shown in an insertion configuration.
Figure 18:
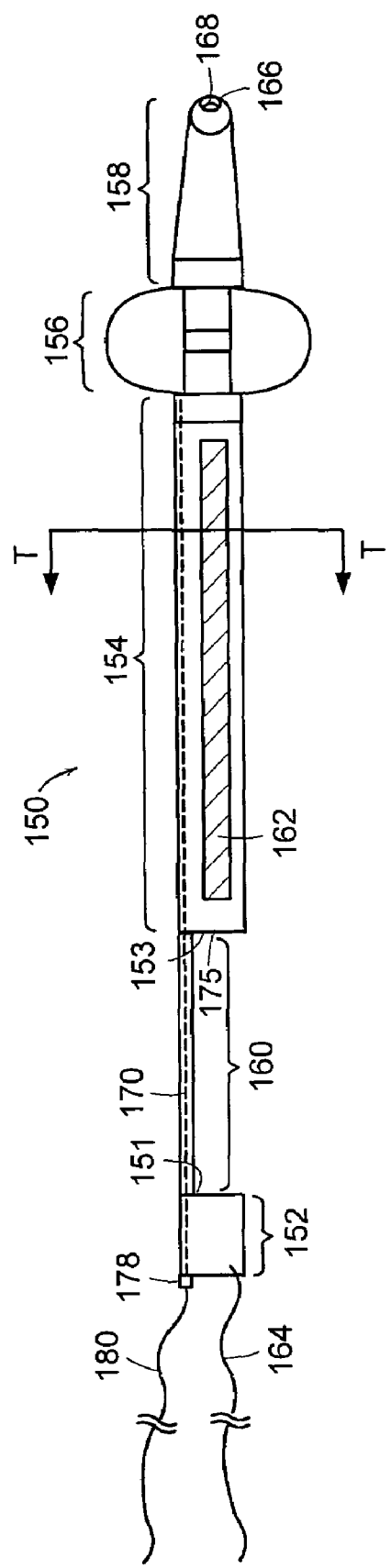
FIG. 18 is a side view of the prostatic stent of FIG. 17A with the inflatable balloon shown in an expanded configuration.

Another embodiment of a prostatic stent 150 is shown in FIGS. 17A and 18. In this embodiment, the prostatic stent 150 includes a bulbar segment 152, a prostatic segment 154, an inflatable balloon 56, a connecting segment 160, and a reinforcing element 162. The bulbar and prostatic segments 152, 154 are tubular elements, each having a lumen sized for conveying fluids. The bulbar and prostatic segments 152, 154 are both made from biocompatible materials, such as silicone, which are sufficiently flexible to conform to the shape of the urethra 106 for insertion ease while simultaneously are also sufficiently rigid to maintain an open passageway through the urethra 106. In the disclosed embodiment, the cross-sectional shape of the bulbar and prostatic segments 152, 154 is circular, however in other embodiments the cross-sectional shape could be elliptical, rectangular, triangular or square.

FIG. 17A shows the prostatic stent 150 in an insertion configuration (with an unfilled inflatable balloon 156). FIG. 18 shows the prostatic stent 150 in an expanded configuration with a filled inflatable balloon 156. To fill the inflatable balloon 156 with a fluid, the prostatic stent 150 includes an inflation channel 170 that extends within the bulbar segment 153 through the connecting segment 160 and the prostatic segment 154 and terminates within the inflatable balloon 156. To accommodate the inflation channel 170, the bulbar segment 152, the connecting segment 160, and the prostatic segment 154 are all integrally connected, creating a continuous path of material to house the inflation channel 170. In the disclosed embodiment, the bulbar segment 152, the connecting segment 160, and the prostatic segment 154 are all formed from a single piece of material such as silicone, although any other biocompatible polymer could also be used as well. In other embodiments, the bulbar, connecting, and prostatic segments 152, 160, 154 can be made from two or more pieces of material that are glued or molded together.

Figure 17B:
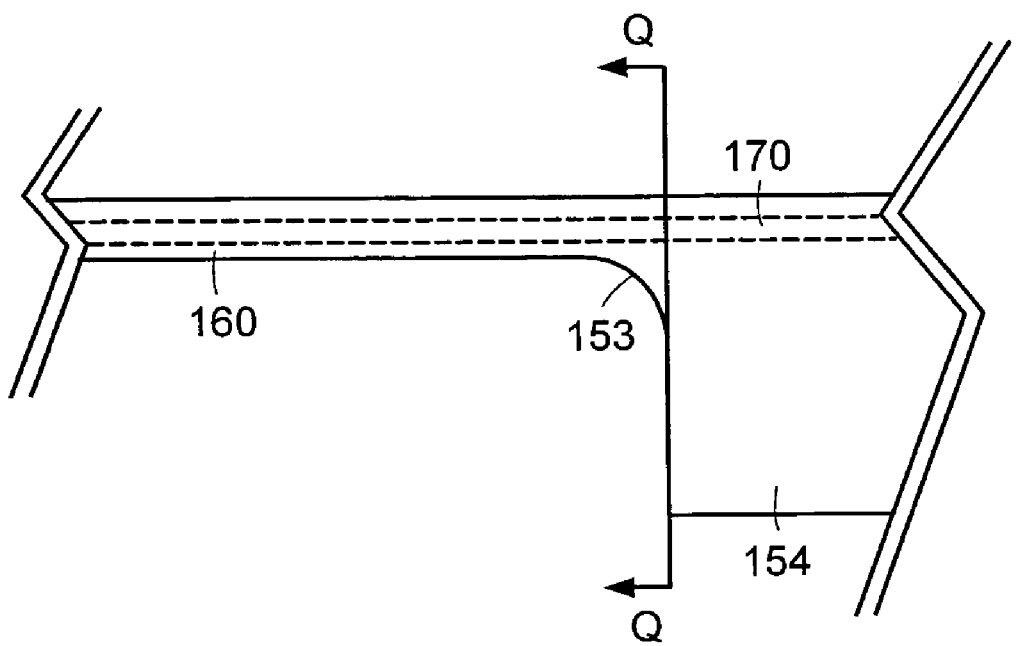
FIG. 17B is an enlarged side view of a section of the prostatic stent shown in FIG. 17A.
Figure 17C:
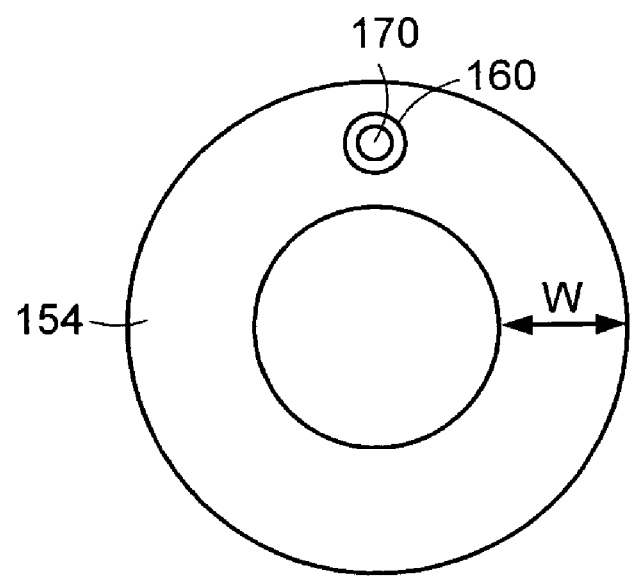
FIG. 17C is an enlarged cross-sectional view of the prostatic stent taken along line QQ in FIG. 17B.
Figure 17D:
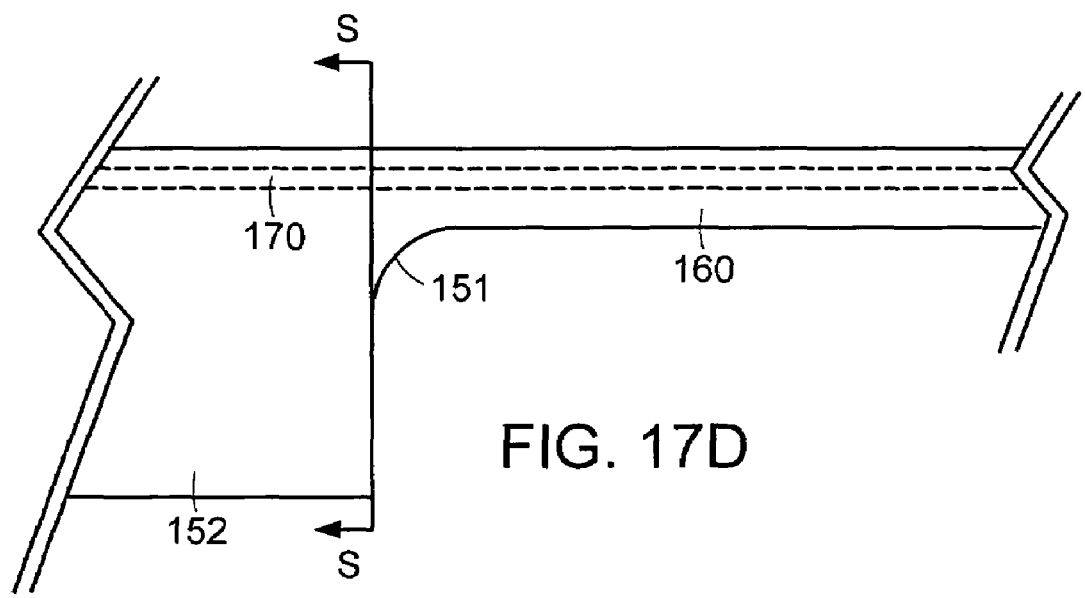
FIG. 17D is another enlarged side view of a section of the prostatic stent shown in FIG. 17A.
Figure 17E:
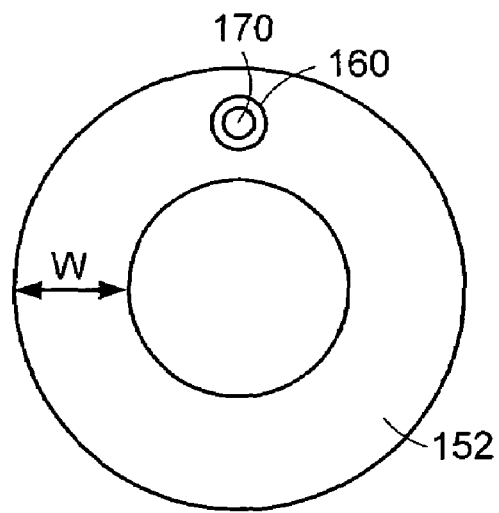
FIG. 17E is an enlarged cross-sectional view of the prostatic stent taken along line SS in FIG. 17D.

Transitions 151,153 between the segments 152, 160, 154 should be smooth and free from jagged surfaces and hanging ends on the exterior surfaces of the segments 152, 160, 154 that would collect blood clots and other debris. FIG. 17B shows an enlarged side view of a section of the prostatic stent 150 labeled P in FIG. 17A. In the disclosed embodiment, the connecting segment 160 and the prostatic segment 154 are integrally connected (i.e., formed from one piece of material) and the transition 153 between the connecting segment 160 and the prostatic segment 154 is free of jagged surfaces and/or rough edges. The inflation channel 170 extends within both the prostatic and connecting segments 154, 160. FIG. 17C, which is a cross-sectional view taken along line QQ in FIG. 17B, shows the location of the inflation channel 170 within the prostatic and connecting segments 154, 160. The bulbar and connecting segments 152, 160 are also integrally connected as shown in FIG. 17D. FIG. 17D is an enlarged side view of a section of the prostatic stent 50 labeled R in FIG. 17A. The location of the inflation channel within the bulbar and connecting segment 152, 160 is shown in FIG. 17E which is an enlarged cross-sectional view taken along line SS in. FIG. 17D.

Figure 19A:
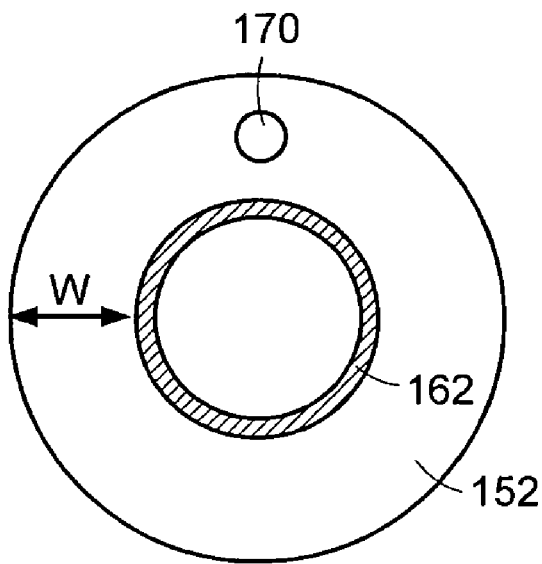
FIG. 19A is an enlarged cross-sectional view of the prostatic stent taken along line TT in FIG. 18 showing a reinforcing element lying against an interior wall of a prostatic segment.
Figure 19B:
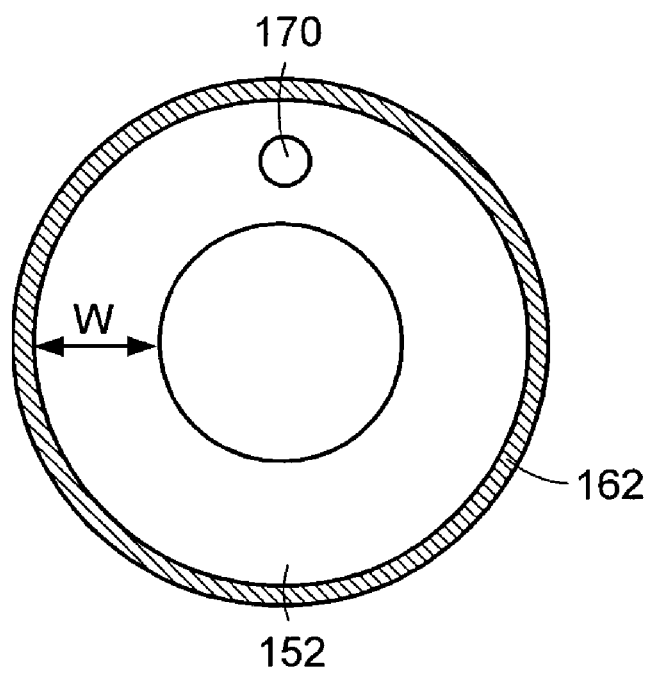
FIG. 19B is another enlarged cross-sectional view taken along line TT in FIG. 18 showing a reinforcing element lying against an exterior wall of the prostatic segment.

Embodiments of reinforcing elements 162 can include a metallic coil or wire mesh tube or other strength-adding member(s) such as, for example, multiple spaced bands of metal to increase the tensile strength of the prostatic segment 154. Generally, the reinforcing element 162 lies against either the interior wall that defines the lumen of the prostatic segment 154 or the exterior wall that defines the outer diameter of the prostatic segment 154, so as not to interfere with the inflation channel 170. FIGS. 19A and B are a cross-sectional views of the prostatic stent 150 taken along line TT in FIG. 17A showing two possible placements of the reinforcing element 162. In FIG. 19A the reinforcing element 162 lies against the interior wall, and in FIG. 19B the reinforcing element lies against the exterior wall. To prevent bodily materials, such as blood clots, from collecting on the reinforcing element 162, the reinforcing element 162 may be coated with silicone or any other biocompatible polymer.

Referring to FIG. 17A, the prostatic stent 150 further includes a proximal tip 158. The proximal tip 158 has a proximal end 166 and can be either straight as shown in FIGS. 17A and 18, or curved. Extending within the proximal tip 158 and the inflatable balloon 156 is a lumen that is in communication with the lumen of the prostatic segment 154. The proximal tip 158 further includes an opening 168 in communication with the lumen extending within the proximal tip 158. The opening 168 is sized to accept fluid from the bladder 100 of the patient, as well as to accept a guide wire. In other embodiments, the proximal tip 158 may include more than one opening 168 in communication with the lumen within the proximal tip 158 to drain fluids such as urine and/or blood from the patient's bladder 100.

Figure 20:
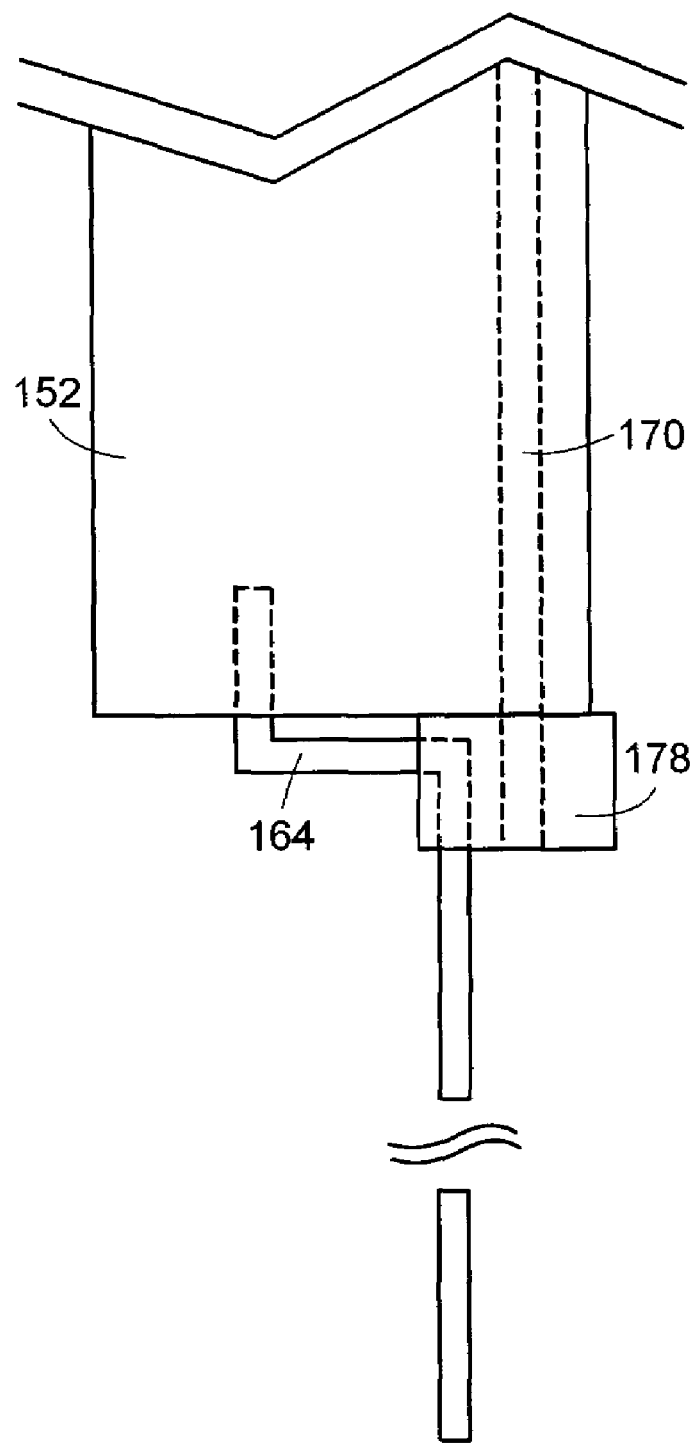
FIG. 20 is an enlarged view of a removal segment embedded within a bulbar segment and within a one-way valve.

Another feature of the prostatic stent 150, as shown in FIG. 17A, is a one way valve 178 located at the end of the inflation channel 170. The one way valve 178 allows fluids such as air or saline to only pass into the inflatable balloon 156. To deflate the inflatable balloon 156 after it has been filled, the one way valve 178 can be removed, thereby allowing the fluid to escape from the inflation channel 170 and the inflatable balloon 156. Attached to the one way valve 178 is a removal suture 180 used for disconnecting the one way valve 178 from the inflation channel 170. To remove the one way valve 178 from the inflation channel 70 the medical professional simply pulls on the removal suture 180. Another element than can be included in the prostatic stent 150 is a removal segment 164, which is a useful tool to a medical professional during placement (i.e., keeping the prostatic and bulbar segments 154,152 properly separated) and removal of the prostatic stent 150 within the body of the patient. In the preferred embodiment, the removal segment 164 would be embedded or secured to the prostatic stent 150 in such a way as to not produce hanging ends or other edges on the exterior surface of the bulbar segment 152 that would collect blood clots or other debris. The end of the removal segment 164 embedded within the bulbar segment 152 may be knotted or folded to provide greater contact surface area between the removal segment 164 and the bulbar segment 152. Referring to FIG. 20, the removal segment 164 can also be embedded to the one way valve 178 and can be used for removing the one way valve 178 from the inflation channel 170 as well as for removing the prostatic stent 150 from the patient's body. To remove the one way valve 178 and the prostatic stent 150 with the removal segment 164, the medical professional uses a two stage pulling process. The medical professional will first pull on the removal segment 164 until he/she senses through tension of the removal segment 164 the release of the one way valve 178. After the one way valve 178 has been removed from the prostatic stent 150, the inflatable balloon 156 will deflate and the medical professional will then be able to pull on the removal segment 164 a second time to remove the prostatic stent 50 from the patient's body.

When the prostatic stent 150 is properly positioned within the patient's urinary system, the inflatable balloon 156 is located within the bladder 100 near the bladder opening, the prostatic segment 154 is located substantially within the prostatic urethra with a distal end 175 of the prostatic segment 154 terminating just prior to the proximal side of the patient's external sphincter 103, and the bulbar segment 152 is located on the distal side of the external sphincter 105. The connecting segment 160 is sized to extend through the external sphincter 104 to attach the bulbar segment 152 to the prostatic segment 154 while not interfering with the normal operation of the external sphincter.

Figure 21:
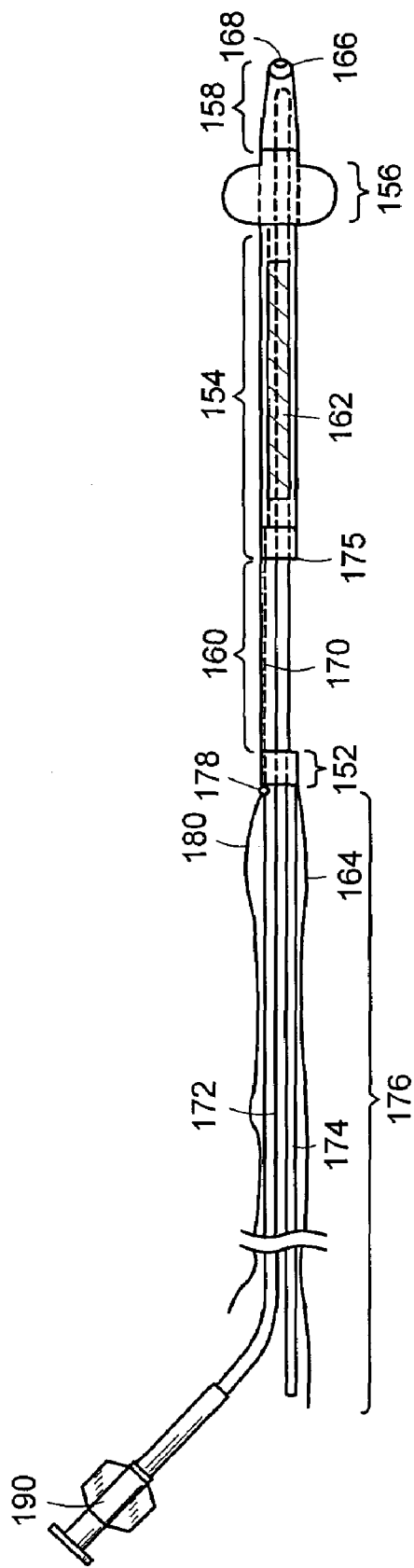
FIG. 21 is a side view of a prostatic stent connected to a delivery system.
Figure 22:
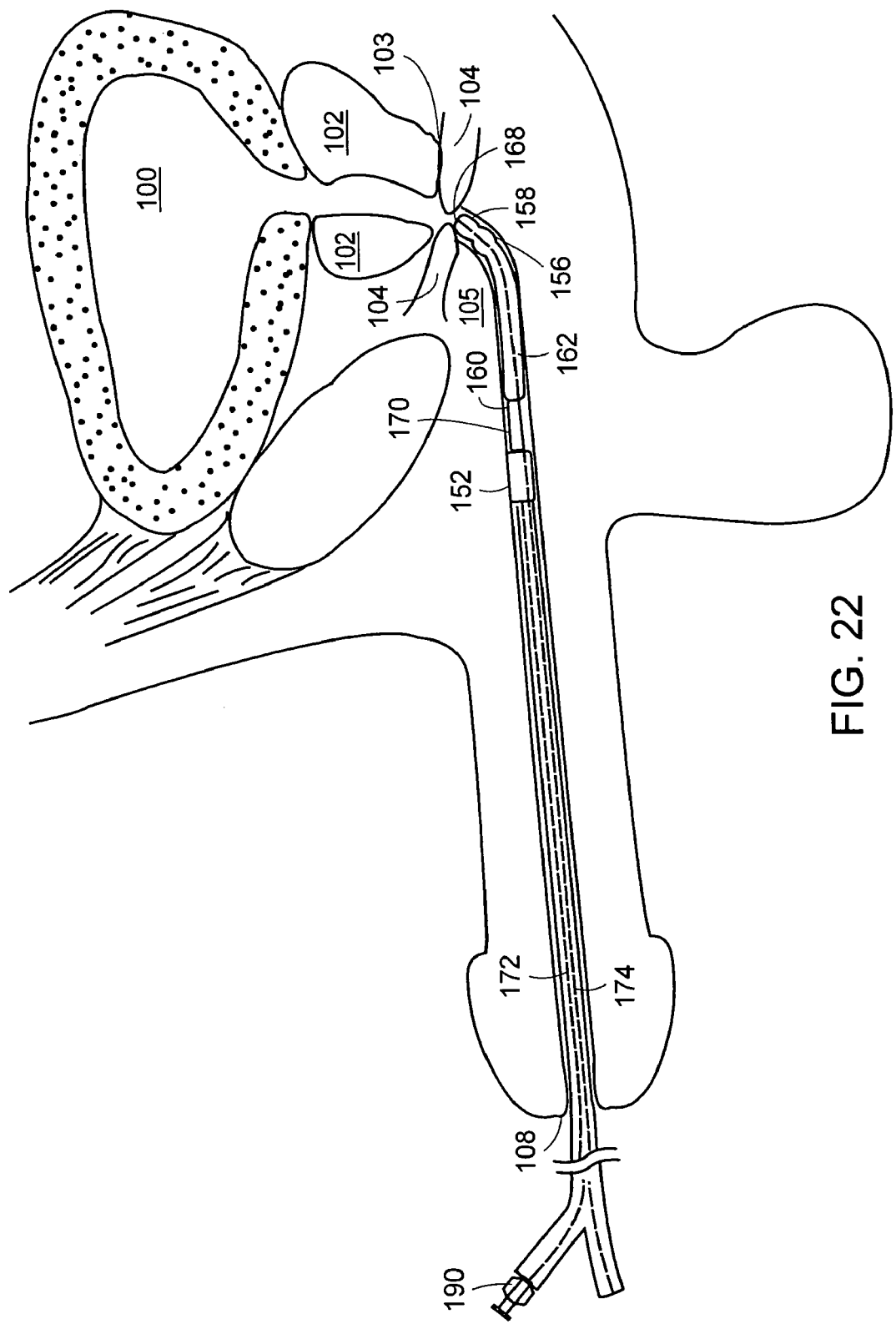
FIG. 22 is a schematic view of a prostatic stent connected to a delivery system being inserted into the male patient's urinary system.
Figure 23:
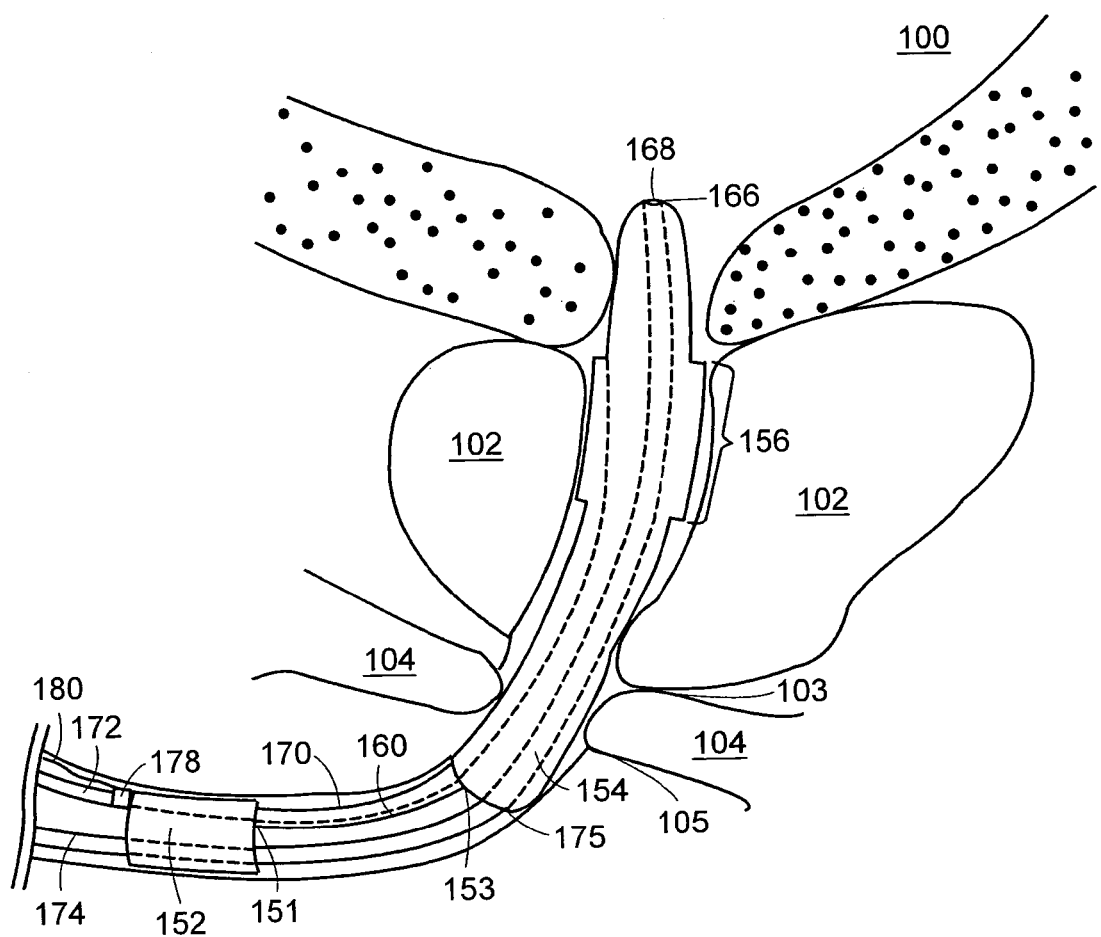
FIG. 23 is an expanded view of a prostatic stent within the male patient's urinary system.

In the disclosed embodiment, a delivery system 176 including a stylet 174 and an inflation line 172 connected to a syringe 190 is used by a physician or other medical professional to properly position the prostatic stent 150 within the urinary system of the patient. In another embodiment, the delivery system 176 could further include a delivery tube similar to the delivery tube 38 shown in FIG. 4. Likewise, the delivery tube would be made from a biocompatible material and would provide rigidity to the delivery system 176. A schematic of the disclosed embodiment of the delivery system 176 used with prostatic stent 150 is shown in FIG. 21. The stylet 174, a long thin member sized to fit within the lumens of the bulbar segment 152 and the prostatic segment 154, is used for advancing the prostatic stent 150 through the patient's urinary system until the inflatable balloon 156 is located within the bladder 100. The inflation line 172 is a tube for conveying fluid from the syringe 190 to the inflation channel 170. Prior to inserting the prostatic stent 150 and the delivery system 176 into the patient's urinary system, the inflation line 172 is connected to the one way valve 178 and the stylet 174 is passed through the lumens of the bulbar and prostatic segments 152, 154 to connect the delivery system 176 to the prostatic stent 150. After the prostatic stent 150 and the delivery system 176 are connected, the medical professional inserts the proximal tip 158 of the prostatic stent 150 into the urethra 106 of the patient at the meatus 108. FIG. 22 shows the prostatic stent 150 in the insertion configuration (unfilled inflatable balloon 156) and the delivery system 176 inserted within the urethra 106. FIG. 23 is an expanded view of the prostatic stent 150 within the area marked H in FIG. 5.

Figure 24:
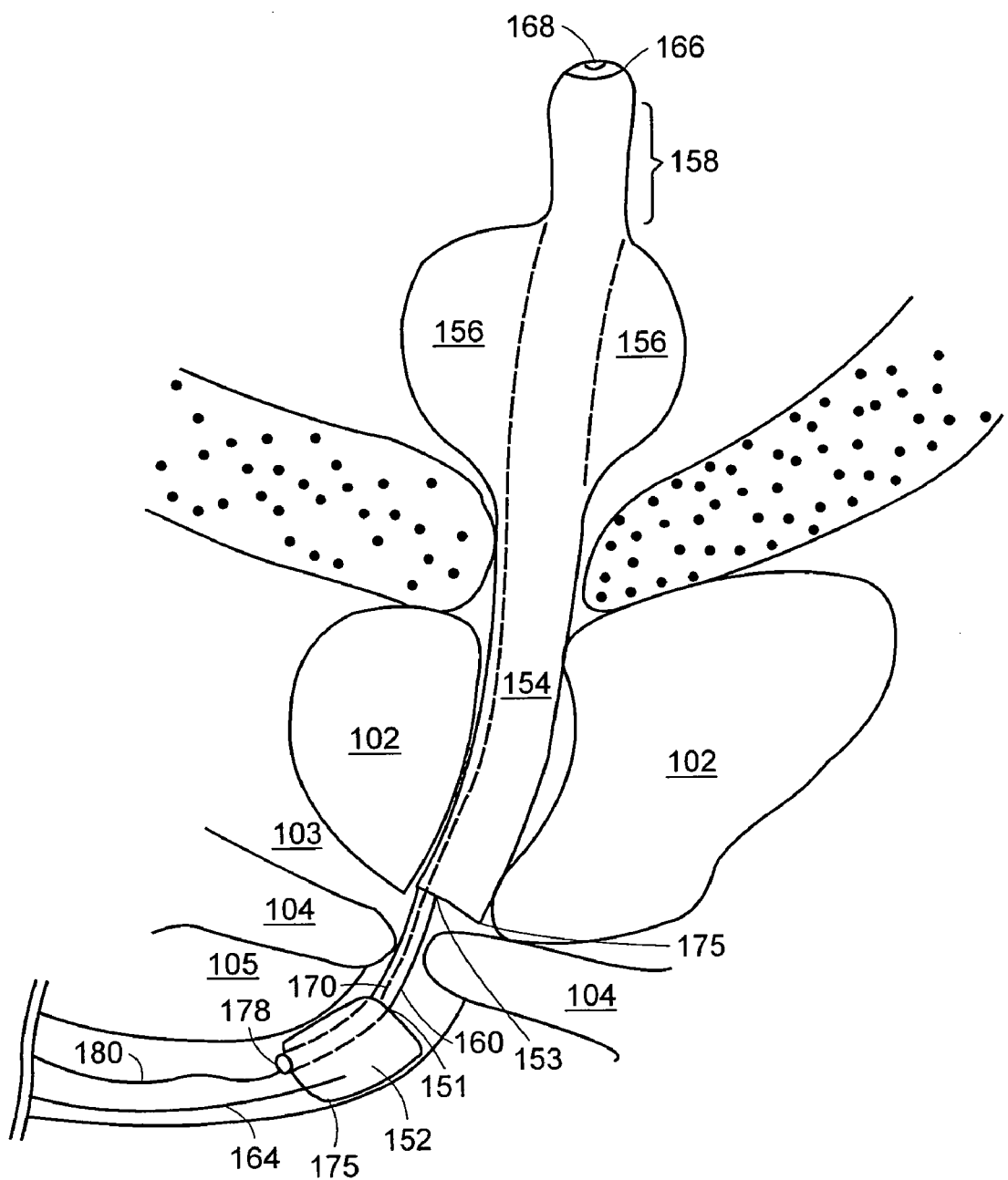
FIG. 24 is another expanded view of a prostatic stent with a inflatable balloon in an expanded configuration and located within the bladder.

It should be noted that the prostatic stent 150 is in the insertion configuration while in this location. The prostatic stent 150 is further advanced through the patient's urethra 106 until the inflatable balloon 156 is within the bladder 100. FIG. 23 shows an expanded view of the prostatic stent 150 within the bladder 100. To confirm placement within the bladder 100, the medical professional looks for urine flowing from an external end of the delivery system 176. Once the inflatable balloon 156 is within the bladder 100, the medical professional uses the syringe 190 to insert a fluid such as saline or air into the inflation line 172. The fluid flows through the inflation line 172, through the one way valve 178 and inflation channel 170, and into the inflatable balloon 156. After the inflatable balloon 156 is filled, the inflation line 172 and stylet 174 are removed from the patient's urethra 106. FIG. 24 shows an expanded view of the prostatic stent 150 within the bladder 100 after the inflatable balloon 156 has been filled (the expanded configuration) and the inflation line 172 and stylet 174 have been removed. The inflatable balloon 156 in the expanded configuration anchors and prevents the distal migration of the prostatic stent 150.

The prostatic stent 150 can be removed from the patient's separately at some later time, by first deflating the inflatable balloon 156, and then removing the prostatic stent 150. To deflate the inflatable balloon 156, the one way valve 178 is disconnected from the prostatic stent 150 by pulling on the removal suture 180. After the one way valve 178 is removed the fluid within the balloon will be able to exit the prostatic stent 150 through the inflation channel 170. With the inflatable balloon 156 deflated, it no longer serves as an anchor to inhibit removal of the prostatic stent 150, and thus the prostatic stent 150 can be removed by either pulling on the removal segment 164 or through endoscopic means.

Variations, modifications, and other implementations of what is described herein will occur to those of ordinary skill in the art without departing from the spirit and the scope of the invention. Accordingly, the invention is not to be limited to only the preceding illustrative description.

What is claimed is:

1. A stent for use in the body of a patient, comprising:
   (a) a first segment locatable on the proximal side of the external sphincter of the patient and including a proximal portion, a distal end, and a lumen extending within the first segment, the proximal portion including at least one opening in communication with the lumen and an inflatable balloon, the inflatable balloon in communication with an inflation channel for conveying fluids to fill the balloon, the inflation channel extending between the inflatable balloon and a valve located on the distal end of the first segment, the valve controlling flow of fluid in and out of the inflation channel, the distal end terminating on the proximal side of the external sphincter when the stent is placed in the body of the patient;
   (b) a second segment locatable on the distal side of the external sphincter of the patient and including a proximal end, a distal end, and a lumen extending within the second segment, the proximal end terminating on the distal side of the external sphincter when the stent is placed in the body of the patient; and
   (c) a connecting member disposed between the first and second segments and coupling together the first and second segments, the connecting member extending from the distal end of the first segment to the proximal end of the second segment with a smooth transition at the distal and proximal ends, the connecting member being sized to extend through the external sphincter and to allow normal operation of the external sphincter by the patient when the stent is placed in the body of the patient.

2. The stent of claim 1 wherein the connecting member comprises a wire with a first end and a second end.

3. The stent according to claim 2 wherein the first and second ends of the wire are embedded in the first and second segments, respectively.

4. The stent of claim 1 wherein the connecting member is integrally connected to the first segment and the second segment.

5. The stent of claim 1 wherein a proximal end of the proximal portion of the first segment is curved.

6. The stent of claim 1 wherein the proximal portion of the first segment includes an additional opening for receiving a guide wire.

7. The stent of claim 1 wherein the first segment farther includes a reinforcing element.

8. The stent of claim 7 wherein the reinforcing element comprises a wire coil.

9. The stent of claim 7 wherein the reinforcing element comprises a wire mesh tube.

10. The stent of claim 1 wherein the second segment further comprises an elongated member extending therefrom and for extension through the urethra and out of the meatus to allow removal of the stent from the body of the patient by pulling on a part of the elongated member external to the body.

11. The stent of claim 10 wherein at least a portion of the elongated member is embedded within the second segment.

12. A stent for use in the body of a patient, comprising:
    (a) a first segment locatable on the proximal side of the external sphincter of the patient and including a proximal portion, a distal end, a reinforcing element, and a lumen extending within the first segment, the proximal portion including at least one opening in communication with the lumen and an inflatable balloon, the distal end of the first segment terminating on the proximal side of the external sphincter when the stent is placed in the body of the patient;
    (b) a second segment locatable on the distal side of the external sphincter of the patient and including a proximal end, a distal end, and a lumen extending within the second segment, the proximal end terminating on the distal side of the external sphincter when the stent is placed in the body of the patient;
    (c) a connecting member disposed between the first and second segments and coupling together the first and second segments, the connecting member extending from the distal end of the first segment to the proximal end of the second segment with a smooth transition at the distal and proximal ends, the connecting member being sized to extend through the external sphincter and to allow normal operation of the external sphincter by the patient when the stent is placed in the body of the patient; and
    (d) an inflation channel for conveying fluid to the inflatable balloon, the inflation channel extending between the inflatable balloon and a valve located on the distal end of the second segment, the valve for controlling the flow of a fluid in and out of the inflation channel.

13. The stent of claim 12 wherein the first segment, the connecting member and the second segment define the inflation channel.

14. The stent of claim 12 wherein the connecting member is integrally connected to the first segment and the second segment.

15. The stent of claim 12 wherein a proximal end of the proximal portion of the first segment is curved.

16. The stent of claim 12 wherein the proximal portion of the first segment includes an additional opening for receiving a guide wire.

17. The stent of claim 12 wherein the reinforcing element comprises a wire coil.

18. The stent of claim 12 wherein the reinforcing element comprises a wire mesh tube.

19. The stent of claim 12 wherein the second segment further comprises an elongated member extending therefrom and for extension through the urethra and out of the meatus to allow removal of the stent from the body of the patient by pulling on a part of the elongated member external to the body.

20. The stent of claim 19 wherein at least a portion of the elongated member is embedded within the second segment.

21. A method of positioning a stent within the urinary system of a patient, the method comprising:
(a) providing a stent comprising: a first segment locatable on the proximal side of the external sphincter of the patient and including a proximal portion, a distal end, and a lumen extending within the first segment, the proximal portion including at least one opening in communication with the lumen and an inflatable balloon, the inflatable balloon in communication with an inflation channel for conveying fluids to fill the balloon, the inflation channel extending between the inflatable balloon and a valve located on the distal end of the first segment, the valve controlling flow of fluid in and out of the inflation channel, the distal end terminating on the proximal side of the external sphincter when the stent is placed in the body of the patient; a second segment locatable on the distal side of the external sphincter of the patient and including a proximal end, a distal end, and a lumen extending within the second segment, the proximal end terminating on the distal side of the external sphincter when the stent is placed in the body of the patient; and a connecting member disposed between the first and second segments and coupling together the first and second segments, the connecting member extending from the distal end of the first segment to the proximal end of the second segment with a smooth transition at the distal and proximal ends, the connecting member being sized to extend through the external sphincter and to allow normal operation of the external sphincter by the patient when the stent is placed in the body of the patient;
(b) providing a stylet for pushing the stent through the patient's urethra, the stylet comprising a proximal end and a distal end, and sized to be received within the lumens of the second and first segments;
(c) providing a syringe and an inflation segment for filling the inflatable balloon with fluid, the inflation segment comprising a first end, a second end, and a lumen extending within the inflation segment;
(d) connecting the first end of the inflation segment to the syringe and the second end to the valve located on the distal end of the first segment;
(e) passing the stylet through the lumens of the second and first segments of the stent;
(f) inserting the stent, stylet, and inflation segment into the patient's urethra;
(g) positioning the stent within the urinary system such that the first segment is located substantially within the prostatic urethra with the proximal portion located within the bladder and the distal end terminating prior to the proximal side of the external sphincter, the second segment located on the distal side of the external sphincter, and the connecting member extending through the external sphincter;
(h) filling the inflatable balloon located within the bladder with the fluid by activating the syringe to force the fluid from the syringe, through the lumen of the inflation segment, through the inflation channel, and into the inflatable balloon;
(i) disconnecting the second end of the inflation segment from the valve located on the distal end of the first segment;
(j) removing the stylet from the first and second segments; and
(k) removing the stylet and inflation segment completely from the patient's urethra, thereby leaving the stent positioned within the patient's urinary system.

22. A method of positioning a stent within the urinary system of a patient, the method comprising:
(a) providing a stent comprising: a first segment locatable on the proximal side of the external sphincter of the patient and including a proximal portion, a distal end, a reinforcing element, and a lumen extending within the first segment, the proximal portion including at least one opening in communication with the lumen and an inflatable balloon, the distal end of the first segment terminating on the proximal side of the external sphincter when the stent is placed in the body of the patient; the second segment locatable on the distal side of the external sphincter of the patient and including a proximal end, the distal end, and a lumen extending within the second segment, the proximal end terminating on the distal side of the external sphincter when the stent is placed in the body of the patient; a connecting member disposed between the first and second segments and coupling together the first and second segments, the connecting member extending from the distal end of the first segment to the proximal end of the second segment with a smooth transition at the distal and proximal ends, the connecting member being sized to extend through the external sphincter and to allow normal operation of the external sphincter by the patient when the stent is placed in the body of the patient; and an inflation channel for conveying fluid to the inflatable balloon, the inflation channel extending between the inflatable balloon and a valve located on the distal end of the second segment, the valve for controlling the flow of a fluid in and out of the inflation channel;
(b) providing a stylet for pushing the stent through the patient's urethra, the stylet comprising a proximal end and a distal end, and sized to be received within the lumens of the second and first segments;
(c) providing a syringe and an inflation segment for filling the inflatable balloon with fluid, the inflation segment comprising a first end, a second end, and a lumen extending within the inflation segment;
(d) connecting the first end of the inflation segment to the syringe and the second end to the valve located on the distal end of the second segment;
(e) passing the stylet through the lumens of the second and first segments of the stent;
(f) inserting the stent, stylet, and inflation segment into the patient's urethra;
(g) positioning the stent within the urinary system such that the first segment is located substantially within the prostatic urethra with the proximal portion located within the bladder and the distal end terminating prior to the proximal side of the external sphincter, the second segment located on the distal side of the external sphincter, and the connecting member extending through the external sphincter;

(h) filling the inflatable balloon located within the bladder with the fluid by activating the syringe to force the fluid from the syringe, through the lumen of the inflation segment, through the inflation channel, and into the inflatable balloon;

(i) disconnecting the second end of the inflation segment from the valve located on the distal end of the second segment;

(j) removing the stylet from the first and second segments; and (k) removing the stylet and inflation segment completely from the patient's urethra, thereby leaving the stent positioned within the patient's urinary system.

* * * * *